(12) United States Patent
Oshiki et al.

(10) Patent No.: US 8,722,912 B2
(45) Date of Patent: May 13, 2014

(54) METAL COMPLEX COMPOUND AND PROCESS FOR PRODUCING AMIDES UTILIZING THE METAL COMPLEX COMPOUND

(75) Inventors: Toshiyuki Oshiki, Okayama (JP); Makoto Muranaka, Okayama (JP)

(73) Assignee: National University Corporation Okayama University (JP)

( * ) Notice: Subject to any disclaimer, the term of this patent is extended or adjusted under 35 U.S.C. 154(b) by 0 days.

(21) Appl. No.: 13/813,725

(22) PCT Filed: Jul. 29, 2011

(86) PCT No.: PCT/JP2011/067531
§ 371 (c)(1),
(2), (4) Date: Feb. 1, 2013

(87) PCT Pub. No.: WO2012/017966
PCT Pub. Date: Feb. 9, 2012

(65) Prior Publication Data
US 2013/0131366 A1 May 23, 2013

(30) Foreign Application Priority Data

Aug. 2, 2010 (JP) .................................. 2010-174025

(51) Int. Cl.
*C07F 9/30* (2006.01)
*C07F 15/00* (2006.01)
*B01J 31/00* (2006.01)
*C07C 231/00* (2006.01)

(52) U.S. Cl.
USPC ............... 556/20; 502/152; 502/155; 556/13; 564/128

(58) Field of Classification Search
USPC ................. 556/13, 20; 502/152, 155; 564/128
See application file for complete search history.

(56) References Cited

U.S. PATENT DOCUMENTS

| | | |
|---|---|---|
| 3,597,481 A | 8/1971 | Tefertiller et al. |
| 3,631,104 A | 12/1971 | Habermann et al. |
| 4,999,443 A | 3/1991 | Bertleff et al. |
| 5,103,065 A | 4/1992 | Bertleff et al. |
| 5,932,756 A | 8/1999 | Parkins et al. |
| 6,133,478 A | 10/2000 | Parkins et al. |

FOREIGN PATENT DOCUMENTS

| | | |
|---|---|---|
| EP | 0175581 A2 | 3/1986 |
| JP | 53039409 B | 10/1978 |
| JP | 61076447 A | 4/1986 |
| JP | 2042093 A | 2/1990 |
| JP | 2008088153 A | 4/2008 |
| JP | 2009023925 A | 2/2009 |
| WO | 9630379 A1 | 10/1996 |

OTHER PUBLICATIONS

Cavarzan, Alessandra et al., "Efficient nitrile hydration mediated by Ru(II) catalysts in micellar media", Green Chemistry, 2010, pp. 790-794, vol. 12, The Royal Society of Chemistry.
Chan, Eddie Y.Y. et al., "Chiral Bisphosphinite Metalloligands Derived from a P-Chiral Secondary Phosphine Oxide", Inorganic Chemistry, 2004, pp. 4921-4926, vol. 43, No. 16, American Chemical Society.
Hunter, Geoffrey et al., "Observation of Slowed Rotation about the n(6)-Arene-Chromium Bond in the Tripodal Chromium Complexes of the Trimers of Bicyclo[2.2.1]hept-2-yne: Intramolecular Rotational Barriers in Organometallic Complexes and their Correlation with Internal Non-bonding Interactions and Structural Changes", Journal of Chem. Soc. Dalton Trans., 1991, pp. 3349-3358.
Klaui, Wolfgang et al., "(Hexamethylbenzene)ruthenium(II) Complexes: Synthesis and Coordination Chemistry of a Novel Tridentate Ligand with an O,O,Cl Donor Set", Inorg. Chem. 1988, pp. 3500-3506, vol. 27, American Chemical Society.
Krafczyk, Roland et al., "Chemistry of bis(pentafluorobenzyl) phosphines and phosphine oxides. Single-crystal X-ray diffraction study of n(6)-mesitylene-dichloro-[bis(pentafluorobenzyl)phosphinous acid]-ruthenium(II) and of 1,2-bis(pentafluorophenyl)ethane", Journal of Fluorine Chemistry, 1997, pp. 159-166, vol. 83, Elsevier Science S.A.
Valderrama, Mauricio et al., "Cationic Homo-and Hetero-binuclear Rutheniurn(II)-Rhodium(III) Complexes with Dimethyl Phosphonate and Halides as Bridging Ligands", J. Chem. Research, 1995, p. 344, No. 9, 1 page.
Yamada, Hideaki et al., "Hydratases Involved in Nitrile Conversion: Screening, Characterization and Application", The Chemical Record, 2001, pp. 152-161, vol. 1, The Japan Chemical Journal Forum and John Wiley & Sons, Inc.

*Primary Examiner* — Porfirio Nazario Gonzalez
(74) *Attorney, Agent, or Firm* — The Webb Law Firm

(57) ABSTRACT

A catalyst contains a metal complex compound represented by the following general formula (I). In the formula (I), M is a metal ion such as ruthenium, $L^1$ is a cyclic or acyclic, neutral or minus 1-valent unsaturated hydrocarbon group of 1 to 30 carbon atoms which may have a substituent, $L^2$ and $L^3$ are each independently chlorine or the like, and $L^4$ is a compound bonded to M through phosphorus or arsenic and represented by the following general formula (IIa) or (IIb). In the formulas (IIa) and (IIb), E is phosphorus or arsenic, $Y^1$ is oxygen or sulfur, $Y^2$, $Y^3$ and $Y^4$ are each independently a hydrogen atom, an aryl group or the like, and H is a hydrogen atom.

23 Claims, 1 Drawing Sheet

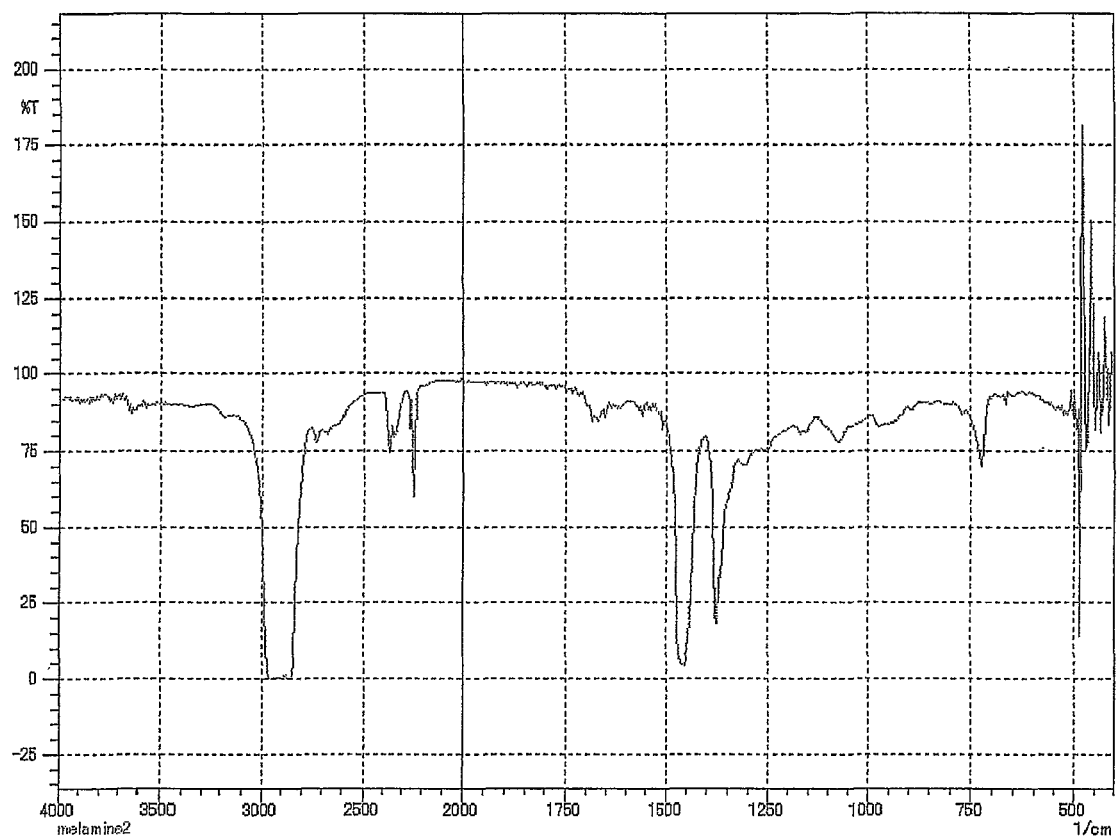

METAL COMPLEX COMPOUND AND PROCESS FOR PRODUCING AMIDES UTILIZING THE METAL COMPLEX COMPOUND

TECHNICAL FIELD

The present invention relates to a metal complex compound, a catalyst containing the metal complex compound and a process for producing amides utilizing catalytic action of the metal complex compound.

BACKGROUND ART

Amides such as acrylamide are important compounds used for various purposes, such as coagulants, paper strength agents, coating materials, agents for crude oil drilling, agents for enhanced oil (crude oil) recovery, lubricants, plasticizers, parting agents and anti-foaming agents. As the process for producing such amides, a process comprising reacting nitriles with water in the presence of a catalyst is known, and a process using a solid catalyst, a biocatalyst or a metal complex catalyst is mainly used.

As the solid catalytic process, for example, a process using a catalyst containing, copper is known (patent literatures 1 and 2), but there are problems that the raw material nitrile needs to be recycled because the conversion of nitrile to amide does not reach 100%, the amide as a product is contaminated with a slight amount of copper ion derived from the catalyst, etc.

On the other hand, as a process overcoming the defects of the solid catalytic process, having a conversion of 100% and being free from contamination with copper ion, a biocatalytic process has been used (non patent literature 1). In the biocatalytic process, however, a large amount of water is necessary in the reaction system because living organisms are used, and in order to obtain amide as crystal, a step and equipment (large amount of energy) for removing the above-mentioned large amount of water become necessary. Further, there is room for improvement in culture and refrigeration of a biocatalyst, complicated thawing conditions, method for removing a biocatalyst from the amide produced, etc.

In addition, as a process using a metal complex catalyst, for example, a process using a platinum phosphine catalyst is known (patent literature 3). Although the platinum catalyst shows high activity, there are problems that the catalyst is expensive, the preparation thereof is complicated, etc. On the other hand, the present inventors have studied processes for synthesizing amide compounds utilizing catalytic action attributed to a combination of a ruthenium complex or an iridium complex and a phosphine compound (patent literatures 4 and 5). Also in the case of the catalyst using the combination of a ruthenium complex or an iridium complex and a phosphine compound, however, there is room for improvement in achievement of reaction under the conditions of lower temperature and smaller amount of thermal energy, yield and purity of the resulting amides (particularly acrylic amides), etc. Recently, a catalyst system in which a ruthenium complex catalyst and a surface active agent are combined has been reported, but the production efficiency (catalytic activity) of amides is extremely low, and the economical efficiency is extremely low (non patent literature 2).

In a non patent literature 3 (compound 8), a ruthenium complex having a phosphine ligand including a pentafluorobenzyl group is disclosed. However, use of the compound, particularly, use of the compound as a catalyst in the production of amides, is neither described nor suggested at all.

CITATION LIST

Patent Literature

Patent literature 1: JP 1986-076447 A
Patent literature 2: JP 1978-039409 A
Patent literature 3: WO96/030379
Patent literature 4: JP 2008-088153 A
Patent literature 5: JP 2009-023925 A

Non Patent Literature

Non patent literature 1: Chemical Record, 2001, 1, 152
Non patent literature 2: Green Chemistry, 2010, 12, 790
Non patent literature 3: Journal of Fluorine Chemistry, 83 (1997), 159-166

SUMMARY OF INVENTION

Technical Problem

The present invention has been made in such circumstances as described above, and it is an object of the present invention to provide a process for producing amides using a metal complex catalyst which has high catalytic activity, is inexpensive and is free from theoretical restrictions of a solid catalytic process (problems such as contamination with a slight amount of copper ion) or a biocatalytic process (problems such as a large amount of water and maintenance of activity of fungus body) during the production, and a metal complex compound used in the process.

Solution to Problem

In order to solve the above problems, the present inventors have earnestly studied, and as a result, they have found that a metal complex compound comprising a given compound has excellent catalytic effects, and they have accomplished the present invention. That is to say, the present invention relates to:

(1) a metal complex compound comprising a compound represented by the following general formula (I):

In the formula (I), M is a metal ion selected from the group consisting of ruthenium, osmium, rhodium, iridium, nickel, palladium and platinum, $L^1$ is a cyclic or acyclic, neutral or minus 1-valent unsaturated hydrocarbon group of 1 to 30 carbon atoms which may have a substituent, $L^2$ and $L^3$ are each independently fluorine, chlorine, bromine, iodine, a hydroxyl group, an alkoxy group which may have a substituent or an aryloxy group which may have a substituent, and $L^4$ is a compound bonded to M through phosphorus or arsenic and represented by the following general formula (IIa) or (IIb):

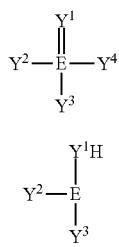

In the formulas (IIa) and (IIb), E is phosphorus or arsenic, $Y^1$ is oxygen or sulfur, $Y^2$, $Y^3$ and $Y^4$ are each independently a hydrogen atom, a hydroxyl group, an alkyl group, an aryl group which may have a substituent and a hetero atom other than carbon, an alkoxy group which may have a substituent or an aryloxy group which may have a substituent, and H is a hydrogen atom.

The metal complex compound has high catalytic activity, is inexpensive and is free from theoretical restrictions of a solid catalytic process (problems such as contamination with a slight amount of copper ion) or a biocatalytic process (problems such as a large amount of water and maintenance of activity of fungus body) during the amide production, and hence, it can be used as a catalyst.

(2) The present invention also relates to a composite constituted of a compound represented by the following general formula (III) and a compound represented by the following general formula (IIa) or (IIb);

In the formula (III), M is a metal ion selected from the group consisting of ruthenium, osmium, rhodium, iridium, nickel, palladium and platinum, $L^1$ is a cyclic or acyclic, neutral or minus 1-valent unsaturated hydrocarbon group of 1 to 30 carbon atoms which may have a substituent, $L^2$ and $L^3$ are each independently fluorine, chlorine, bromine, iodine, a hydroxyl group, an alkoxy group which may have a substituent or an aryloxy group which may have a substituent, and when the valence of M is +1 or +2, $L^3$ is not present in some cases and the compound represented by the general formula (III) may form an associate,

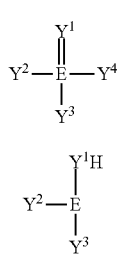

In the formulas (IIa) and (IIb), E is phosphorus or arsenic, $Y^1$ is oxygen or sulfur, $Y^2$, $Y^3$ and $Y^4$ are each independently a hydrogen atom, a hydroxyl group, an alkyl group, an aryl group which may have a substituent and a hetero atom other than carbon, an alkoxy group which may have a substituent or an aryloxy group which may have a substituent, and H is a hydrogen atom.

(3) In the compounds as stated in the above (1) and (2), $L^1$ may be cyclic diene, triene or tetraene of 1 to 30 carbon atoms which may have a substituent and is a neutral or minus 1-valent unsaturated hydrocarbon group.

(4) In the compounds as stated in the above (1) and (2), $L^1$ may be acyclic diene, triene or tetraene of 1 to 30 carbon atoms which may have a substituent and is a neutral or minus 1-valent unsaturated hydrocarbon group.

(5) In the compounds as stated in the above (1) and (2), $L^4$, that is, the compound represented by the general formula (IIa) or (IIb) may be any one of secondary phosphine oxide, an aliphatic phosphoric acid ester, an aliphatic phosphorous acid ester, an aromatic phosphoric acid ester and an aromatic phosphorous acid ester of 1 to 30 carbon atoms which may have a substituent.

(6) $L^4$ in the compounds as stated in the above (5), that is, the compound represented by the general formula (IIa) or (IIb) may be any one of diarylphosphine oxide which may have a substituent, dialkylphosphine oxide, secondary phosphine oxide having a phenyl group which may have a substituent and having an alkyl group which may have a substituent, a phosphorous acid dialkyl ester of 1 to 30 carbon atoms, a phosphorous acid diphenyl ester which may have a substituent and a phosphorous acid ester having a phenyl group which may have a substituent and having an alkyl group which may have a substituent.

(7) The present invention also provides a catalyst comprising the metal complex compound as stated in the above (1) or the composite as stated in the above (2).

(8) The catalyst as stated in the above (7) can be used for hydration reaction.

(9) The hydration catalyst as stated in the above (8) may be a catalyst further comprising a reaction accelerator in addition to the metal complex compound as stated in the above (1) or (2).

(10) In the hydration catalyst as stated in the above (9), the reaction accelerator may be any one of diphenylphosphine oxide which may have a substituent, dialkylphosphine oxide, phosphine oxide having a phenyl group which may have a substituent or an alkyl group which may have a substituent, a phosphorous acid dialkyl ester of 1 to 30 carbon atoms, a phosphorous acid diphenyl ester which may have a substituent, a phosphorous acid ester having a phenyl group which may have a substituent and having an alkyl group which may have a substituent, an aliphatic alcohol which may have a substituent, an aromatic alcohol which may have a substituent, an aliphatic carboxylic acid which may have a substituent and an aromatic carboxylic acid which may have a substituent.

(11) The hydration catalyst as stated in the above (9) may be a catalyst containing the reaction accelerator in an amount of 1 to 100 mol based on 1 mol of the metal complex compound represented by the general formula (I) or the compound represented by the general formula (II).

(12) The hydration catalyst as stated in the above (8) to (11) can be effectively used for, for example, hydration of nitriles.

(13) The present invention also provides a process for producing amides, comprising a step of preparing a catalyst comprising the metal complex compound as stated in the above (1) or (2), a step of adding the catalyst to a mixture of a nitrile and water and/or an organic solvent, and a step of reacting the mixture containing the catalyst at a temperature of 0 to 150° C. for 0.1 to 48 hours. By the use of such reaction conditions, amides can be efficiently produced.

(14) In the process for producing amides as stated in the above (13), the nitrile may be an aliphatic nitrile of 1 to 30 carbon atoms which may have a substituent.

(15) In the process for producing amides as stated in the above (13), the nitrile may be an aromatic nitrile of 1 to 30 carbon atoms which may have a substituent.

(16) In the process for producing amides as stated in the above (14), the nitrile may be any one of acrylonitrile, methacrylonitrile, polyacrylonitrile and polymethacrylonitrile.

By the use of the metal complex compound provided by the present invention, it becomes possible to inexpensively produce amides with high catalytic activity and without theoretical restrictions of a solid catalytic process (problems such as contamination with a slight amount of copper ion) or a biocatalytic process (problems such as a large amount of water and maintenance of activity of fungus body) during the amide production.

BRIEF DESCRIPTION OF DRAWING

The drawing depicts an infrared absorption spectrum of polyacrylamide produced in Example 9-7 of the present invention.

DETAILED DESCRIPTION OF EMBODIMENTS

The present invention is described in detail hereinafter.

In one aspect, the present invention provides a metal complex compound represented by the following general formula (I) (sometimes referred to as a "metal complex compound (I)" hereinafter).

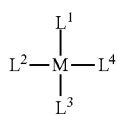
(I)

Here, M in the general formula (I) is a metal ion selected from the group consisting of ruthenium, osmium, rhodium, iridium, nickel, palladium and platinum.

$L^1$ is a cyclic or acyclic, neutral or minus 1-valent unsaturated hydrocarbon group of 1 to 30 carbon atoms which may have a substituent, and examples thereof include ethylene, propylene, isoprene, butadiene, 2,3-dimethyl-1,3-butadiene, cyclohexene, acetylene, propyne, phenylacetylene, trimethylsilylpropyne, phenylpropyne, diphenylacetylene, pyridine, 4,4-dimethylaminopyridine, imidazole, acetonitrile, benzonitrile, butadiene, 1,4-diphenyl-1,3-butadiene, cyclooctene, 1,5-cyclooctadiene, norbornadiene, benzene, hexamethylbenzene, p-cymene, anisole, naphthalene, methylnaphthalene, cyclooctatetraene, cyclopentadiene, methylcyclopentadiene, 1,2-dimethylcyclopentadiene, 1,4-dimethylcyclopentadiene, pentamethylcyclopentadiene, indene and methylindene.

The bond between M and $L^1$ may be any one of covalent bond, ionic bond and coordinate bond. The line connecting M to $L^1$ in the general formula (I) indicates that M and $L^1$ are bonded by any one of the above bonds, and the line is not limited to the case where $L^1$ is in a monodentate coordination mode. For example, when $L^1$ is cyclooctene, it is bonded to M by coordinate bond and monodentate coordination, when $L^1$ is cyclooctadiene, it is bonded to M by coordinate bond and bidentate coordination, and when $L^1$ is a cyclopentadienyl group, it is bonded to M by covalent bond and tridentate coordination, so that the line connecting M to $L^1$ in the general formula (I) includes the bond in any of these cases.

$L^2$ and $L^3$ are each independently hydrogen, fluorine, chlorine, bromine, iodine, a hydroxyl group, an alkoxy group which may have a substituent or an aryloxy group which may have a substituent. The alkoxy group or the aryloxy group is, for example, a group represented by the general formula —OR or a group represented by the general formula —OCOR (acyloxy group). Here, R in these formulas is selected from the group consisting of hydrogen, a saturated or unsaturated, straight-chain or branched hydrocarbon group of 1 to 30 carbon atoms, a saturated or unsaturated cyclic hydrocarbon group of 1 to 30 carbon atoms, an aromatic compound residue of 6 to 30 carbon atoms, an alkoxy group and an aryloxy group. Examples of the alkoxy groups which may have a substituent include methoxy group, ethoxy group, n-propoxy group, isopropoxy group, butoxy group, isobutoxy group, hydroxymethoxy group, chloromethoxy group, 2-hydroxyethoxy group, 2-fluoroethoxy group and 2-chloroethoxy group; and examples of the acyloxy groups which may have a substituent include —OCOCH$_3$, —OCOC$_2$H$_5$, —OCOC$_3$H$_7$, —OCOCF$_3$, —OCOC$_6$H$_5$ and —OCOC$_6$F$_5$. As examples of $L^2$ and/or $L^3$, bidentate ligands such as an acetylacetonato group which may have a substituent can be also given. Examples of the substituents of the acetylacetanoto group include methyl group, ethyl group, phenyl group and fluoro group. Examples of the acetylacetonato groups which may have a substituent include 1,3-diphenyl-1,3-propanedionato group, 2,2,6,6-tetramethyl-3,5-heptanedionato group and hexafluoroacetylacetonato group. As other examples of $L^2$ and $L^3$, —OSO$_2$CF$_3$ and —OSO$_2$CH$_3$ can be also given.

The bond between M and each of $L^2$ and $L^3$ may also be any of covalent bond, ionic bond and coordinate bond. The line connecting M to each of $L^2$ and $L^3$ in the general formula (I) indicates that M and each of $L^2$ and $L^3$ are bonded by any one of the above bonds, and the line is not limited to the case where $L^2$ and $L^3$ are each in a monodentate coordination mode. For example, $L^2$ such as acetylacetonato group undergoes, as a bidentate ligand, coordinate bonding to M by two oxygen atoms, and the line connecting M to $L^2$ in the general formula (I) also includes the bond in such a case.

$L^4$ is a compound bonded to M through phosphorus or arsenic and represented by the general formula (IIa) or (IIb) (sometimes referred to as a "compound (IIa)" or a "compound (IIb)" hereinafter). In the compound (IIb), a tautomer of the compound (IIa) is included. For example, when the metal complex compound (I) is isolated, the compound (IIb) can exist as a tautomer of the compound (IIa).

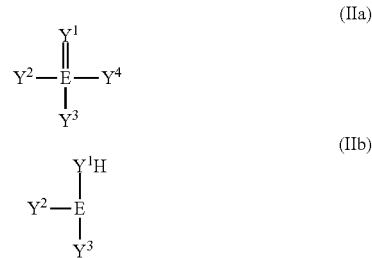

In the formulas (IIa) and (IIb), E is phosphorus or arsenic, and $Y^1$ is oxygen or sulfur. $Y^2$, $Y^3$ and $Y^4$ are each independently a hydrogen atom, a hydroxyl group, an alkyl group (e.g., methyl group, ethyl group, n-propyl group, 1-propyl group, n-butyl group, i-butyl group, t-butyl group, n-hexyl group, n-octyl group), an aryl group (e.g., phenyl group) which may have a substituent and a hetero atom other than carbon, or an aryloxy group (e.g., phenoxy group) which may have a substituent. The number of carbon atoms in the alkyl group, the aryl group, the alkoxy group or the aryloxy group is usually 1 to 30. Examples of the substituents include hydroxyl group, amino group, carboxyl group and mercapto group.

Examples of the compounds (IIa) and (IIb) include phenylphosphinic acid, diphenylphosphine oxide, di(4-methylphenyl)phosphine oxide, di(3-methylphenyl)phosphine oxide, di(2-methylphenyl)phosphine oxide, di(4-fluorophenyl)phosphine oxide, di(3-trifluoromethylphenyl)phosphine oxide, di(2-trifluoromethylphenyl)phosphine oxide, di(tetrafluoropyridyl)phosphineoxide, dimethylphosphineoxide, diethylphosphine oxide, di-n-butylphosphine oxide, di-t-butylphosphine oxide, di-n-pentylphosphine oxide, methylphenylphosphine oxide, ethylphenylphosphine oxide, t-butylmethylphosphine oxide, diethyl phosphite, dibutyl phosphite, diisobutyl phosphite, di-t-butyl phosphite, diphenyl phosphite, phenylphosphinic acid, 1,3-dimethyl-1,3,2-diazaphospholidin-2-one, 1,3,2-diazaphospholidine 1,3-diphenyl-2-oxide, 1,3-di-t-butyl-1,3-2-diazaphospholidine 2-oxide 1,3, 2-diazaphospholidine, 1,3-bis[2,6-bis(1-methylethyl)phenyl]-2-oxide, 1,3,2-diazaphospholidine, 1,3-dibutyl-2-oxide 1,3,2-diazaphospolidine and 1,3-bis(1-methylpropyl)-2-oxidodiphenylphosphine sulfide.

Examples of the metal complex compounds (I) include the following compounds:

benzene ruthenium dichloride diphenylhydroxyphosphine, benzene ruthenium dibromide diphenylhydroxyphosphine, benzene ruthenium diiodide diphenylhydroxyphosphine, hexamethylbenzene ruthenium dichloride diphenylhydroxyphosphine, hexamethylbenzene ruthenium dibromide diphenylhydroxyphosphine, hexamethylbenzene ruthenium diiodide diphenylhydroxyphosphine, (p-cymene)ruthenium dichloride diphenylhydroxyphosphine, (p-cymene)ruthenium dibromide diphenylhydroxyphosphine, (p-cymene)ruthenium diiodide diphenylhydroxyphosphine, benzene ruthenium dichloride di-n-butylhydroxyphosphine, benzene ruthenium dibromide di-n-butylhydroxyphosphine, benzene ruthenium diiodide di-n-butylhydroxyphosphine, hexamethylbenzene ruthenium dichloride di-n-butylhydroxyphosphine, hexamethylbenzene ruthenium dibromide di-n-butylhydroxyphosphine, hexamethylbenzene ruthenium diiodide di-n-butylhydroxyphosphine, (p-cymene)ruthenium dichloride di-n-butylhydroxyphosphine, (p-cymene)ruthenium dibromide di-n-butylhydroxyphosphine, (p-cymene)ruthenium diiodide di-n-butylhydroxyphosphine, benzene ruthenium dichloride diisobutylhydroxyphosphine, benzene ruthenium dibromide diisobutylhydroxyphosphine, benzene ruthenium diiodide diisobutylhydroxyphosphine, hexamethylbenzene ruthenium dichloride dibutylhydroxyphosphine, hexamethylbenzene ruthenium dibromide dibutylhydroxyphosphine, hexamethylbenzene ruthenium diiodide diisobutylhydroxyphosphine, (p-cymene)ruthenium dichloride diisobutylhydroxyphosphine, (p-cymene)ruthenium dibromide dibutylhydroxyphosphine, (p-cymene)ruthenium diiodide dibutylhydroxyphosphine, benzene ruthenium dichloride dimethylhydroxyphosphine, benzene ruthenium dibromide dimethylhydroxyphosphine, benzene ruthenium diiodide dimethylhydroxyphosphine, hexamethylbenzene ruthenium dichloride dimethylhydroxyphosphine, hexamethylbenzene ruthenium dibromide dimethylhydroxyphosphine, hexamethylbenzene ruthenium diiodide dimethylhydroxyphosphine, (p-cymene)ruthenium dichloride dimethylhydroxyphosphine, (p-cymene)ruthenium dibromide dimethylhydroxyphosphine, (p-cymene)ruthenium diiodide dimethylhydroxyphosphine, benzene ruthenium dichloride diethylhydroxyphosphine, benzene ruthenium dibromide diethylhydroxyphosphine, benzene ruthenium diiodide diethylhydroxyphosphine, hexamethylbenzene ruthenium dichloride diethylhydroxyphosphine, hexamethylbenzene ruthenium dibromide diethylhydroxyphosphine, hexamethylbenzene ruthenium diiodide diethylhydroxyphosphine, (p-cymene)ruthenium dichloride diethylhydroxyphosphine, (p-cymene)ruthenium dibromide diethylhydroxyphosphine, (p-cymene)ruthenium diiodide diethylhydroxyphosphine, cyclopentadienyl iridium dichloride diphenylhydroxyphosphine, cyclopentadienyl iridium dibromide diphenylhydroxyphosphine, cyclopentadienyl iridium diiodide diphenylhydroxyphosphine, methylcyclopentadienyl iridium dichloride diphenylhydroxyphosphine, methylcyclopentadienyl iridium dibromide diphenylhydroxyphosphine, methylcyclopentadienyl iridium diiodide diphenylhydroxyphosphine, dimethylcyclopentadienyl iridium dichloride diphenylhydroxyphosphine, dimethylcyclopentadienyl iridium dibromide diphenylhydroxyphosphine, dimethylcyclopentadienyl iridium diiodide diphenylhydroxyphosphine, pentamethylcyclopentadienyl iridium dichloride diphenylhydroxyphosphine, pentamethylcyclopentadienyl iridium dibromide diphenylhydroxyphosphine, pentamethylcyclopentadienyl iridium diiodide diphenylhydroxyphosphine, indenyl iridium dichloride diphenylhydroxyphosphine, indenyl iridium dibromide diphenylhydroxyphosphine, indenyl iridium diiodide diphenylhydroxyphosphine, cyclopentadienyl iridium dichloride di-n-butylhydroxyphosphine, cyclopentadienyliridium dibromide di-n-butylhydroxyphosphine, cyclopentadienyl iridium diiodide di-n-butylhydroxyphosphine, methylcyclopentadienyl iridium dichloride di-n-butylhydroxyphosphine, methylcyclopentadienyl iridium dibromide di-n-butylhydroxyphosphine, methylcyclopentadienyl iridium diiodide di-n-butylhydroxyphosphine, dimethylcyclopentadienyl iridium dichloride di-n-butylhydroxyphosphine, dimethylcyclopentadienyl iridium dibromide di-n-butylhydroxyphosphine, dimethylcyclopentadienyl iridium diiodide di-n-butylhydroxyphosphine, pentamethylcyclopentadienyl iridium dichloride di-n-butylhydroxyphosphine, pentamethylcyclopentadienyl iridium dibromide di-n-butylhydroxyphosphine, pentamethylcyclopentadienyl iridium diiodide di-n-butylhydroxyphosphine, indenyl iridium dichloride di-n-butylhydroxyphosphine, indenyl iridium dibromide di-n-butylhydroxyphosphine, indenyl iridium diiodide di-n-butylhydroxyphosphine, cyclopentadienyl iridium dichloride diisobutylhydroxyphosphine, cyclopentadienyl iridium dibromide diisobutylhydroxyphosphine, cyclopentadienyl iridium diiodide diisobutylhydroxyphosphine, methylcyclopentadienyl iridium dichloride dibutylhydroxyphosphine, methylcyclopentadienyl iridium dibromide dibutylhydroxyphosphine, methylcyclopentadienyl iridium diiodide diisobutylhydroxyphosphine, dimethylcyclopentadienyl iridium ruthenium dichloride diisobutylhydroxyphosphine, dimethylcyclopentadienyl iridium dibromide diisobutylhydroxyphosphine, dimethylcyclopentadienyl iridium diiodide diisobutylhydroxyphosphine, pentamethylcyclopentadienyl iridium dichloride diisobutylhydroxyphosphine, pentamethylcyclopentadienyl iridium dibromide diisobutylhydroxyphosphine, pentamethylcyclopentadienyl iridium diiodide diisobutylhydroxyphosphine, indenyl iridium dichloride diisobutylhydroxyphosphine, indenyl iridium dibromide diisobutylhydroxyphosphine, indenyl iridium diiodide diisobutylhydroxyphosphine, cyclopentadienyl iridium dichloride dimethylhydroxyphosphine, cyclopentadienyl iridium dibromide dimethylhydroxyphosphine, cyclopentadienyl iridium diiodide dimethylhydroxyphosphine, methylcyclopentadienyl iridium dichloride dimethylhydroxyphosphine, methylcyclopentadienyl iridium dibromide dimethylhydroxyphosphine, methylcyclopentadienyl iridium diiodide dimethylhydroxyphosphine, dimethylcyclopentadienyl iridium dichloride dimethylhydroxyphosphine, dimethylcyclopentadienyl iridium dibromide dimethylhydroxyphosphine, dimethylcyclopentadienyl iridium diiodide dimethylhydroxyphosphine, pentamethylcyclopentadienyl iridium dichloride dimethylhydroxyphosphine, pentamethylcyclopentadienyl iridium dibromide dimethylhydroxyphosphine, pentamethylcyclopentadienyl iridium diiodide dimethylhydroxyphosphine, indenyl iridium dichloride dimethylhydroxyphosphine, indenyl iridium dibromide dimethylhydroxyphosphine, indenyl iridium diiodide dimethylhydroxyphosphine, cyclopentadienyl iridium dichloride diethylhydroxyphosphine, cyclopentadienyl iridium dibromide diethylhydroxyphosphine, cyclopentadienyl iridium diiodide diethylhydroxyphosphine, cyclopentadienyl iridium dichloride diethylhydroxyphosphine, cyclopentadienyl iridium dibromide diethylhydroxyphosphine, cyclopentadienyl iridium diiodide diethylhydroxyphosphine, methylcyclopentadienyl iridium dichloride diethylhydroxyphosphine, methylcyclopentadienyl iridium dibromide diethylhydroxyphosphine, methylcyclopentadienyl iridium diiodide diethylhydroxyphosphine, pentamethylcyclopentadienyl iridium dichloride diethylhydroxyphosphine, pentamethylcyclopentadienyl iridium dibromide diethylhydroxyphosphine, pentamethylcyclopentadienyl iridium diiodide diethylhydroxyphosphine, indenyl iridium dichloride diethylhydroxyphosphine, indenyl iridium dibromide diethylhydroxyphosphine and indenyl iridium diiodide diethylhydroxyphosphine.

In another aspect, the present invention provides a substance obtained by mixing a compound represented by the general formula (III) with a compound represented by the general formula (IIa) or (IIb), that is, a mixture in which these compounds are in a mixed state, a compound in which these compounds are in a chemically bonded state, an associate in which these compounds are bonded by intermolecular force, or the like. In the present invention, the mixture, the compound and the associate are generically referred to as "composite". The aforesaid metal complex compound (I) is included as one embodiment of the above compound. In the present invention, the compound (III) and the compound (IIa) or (IIb) (particularly the compound (IIa)) can exhibit catalytic activity even if they are in a mixed state where formation of a specific compound or an associate is not confirmed.

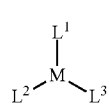

(III)

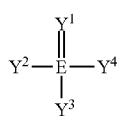

(IIa)

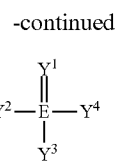

(IIb)

In the formula (III), definitions of M, $L^1$, $L^2$ and $L^3$ are the same as those of the compound represented by the general formula (I). The bond between M and each of $L^1$, $L^2$ and $L^3$ may also be any of covalent bond, ionic bond and coordinate bond similarly to that in the general formula (I). The line connecting M to each of $L^1$, $L^2$ and $L^3$ in the general formula (III) indicates that M and each of $L^1$, $L^2$ and $L^3$ are bonded by any one of the above bonds, and the line is not limited to the case where $L^1$, $L^2$ and $L^3$ are each in a monodentate coordination mode. In the general formula (III), $L^3$ is not present in some cases depending upon the valence of M (that is, when the valence of M is +1 or +2).

The compounds represented by the general formula (III) may form together such an associate as represented by the following formula (IV).

(IV)

Examples of ruthenium compounds represented by the general formula (III) include benzene ruthenium dichloride, methylbenzene ruthenium dichloride, hexamethylbenzene ruthenium dichloride, (p-cymene)ruthenium dichloride, methoxybenzene ruthenium dichloride, ethoxybenzene ruthenium dichloride, hydroxybenzene ruthenium dichloride, naphthalene ruthenium dichloride, methylnaphthalene ruthenium dichloride, 2-phenoxyethanol ruthenium dichloride, benzene ruthenium dibromide, methylbenzene ruthenium dibromide, hexamethylbenzene ruthenium dibromide, (p-cymene)ruthenium dibromide, methoxybenzene ruthenium dibromide, ethoxybenzene ruthenium dibromide, hydroxybenzene ruthenium dibromide, naphthalene ruthenium dibromide, methylnaphthalene ruthenium dibromide, 2-phenoxyethanol ruthenium dibromide, benzene ruthenium diiodide, methylbenzene ruthenium diiodide, hexamethylbenzene ruthenium diiodide, (p-cymene)ruthenium diiodide, methoxybenzene ruthenium diiodide, ethoxybenzene ruthenium diiodide, hydroxybenzene ruthenium diiodide, naphthalene ruthenium diiodide, methylnaphthalene ruthenium diiodide, 2-phenoxyethanol ruthenium diiodide, benzene ruthenium difluoride, methylbenzene ruthenium difluoride, hexamethylbenzene ruthenium difluoride, (p-cymene)ruthenium difluoride, methoxybenzene ruthenium difluoride, ethoxybenzene ruthenium difluoride, hydroxybenzene ruthenium difluoride, naphthalene ruthenium difluoride, methylnaphthalene ruthenium difluoride, 2-phenoxyethanol ruthenium difluoride, benzene ruthenium dihydride, methylbenzene ruthenium dihydride, hexamethylbenzene ruthenium dihydride, (p-cymene)ruthenium dihydride, methoxybenzene ruthenium dihydride, ethoxybenzene ruthenium dihydride, hydroxybenzene ruthenium dihydride, naphthalene ruthenium dihydride, methylnaphthalene ruthenium dihydride, 2-phenoxyethanol ruthenium dihydride, cyclooctatetraene ruthenium dichloride, norbornadiene ruthenium dichloride, cyclpentadienyl ruthenium dichloride, methylcyclopentadienyl ruthenium dichloride, pentamethylcyclopentadienyl ruthenium dichloride, pyrrolyl ruthenium dichloride, methylpyrrolyl ruthenium dichloride, cyclopentadienyl ruthenium dibromide, methylcyclopentadienyl ruthenium dibromide, pentamethylcyclopentadienyl ruthenium dibromide, pyrrolyl ruthenium dibromide, methylpyrrolyl ruthenium dibromide, cyclopentadienyl ruthenium diiodide, methylcyclopentadienyl ruthenium diiodide, pentamethylcyclopentadienyl ruthenium diiodide, pyrrolyl ruthenium diiodide, methylpyrrolyl ruthenium diiodide, cyclopentadienyl ruthenium difluoride, methylcyclopentadienyl ruthenium difluoride, pentamethylcyclopentadienyl ruthenium difluoride, pyrrolyl ruthenium difluoride, methylpyrrolyl ruthenium difluoride, cyclopentadienyl ruthenium dihydride, methylcyclopentadienyl ruthenium dihydride, pentamethylcyclopentadienyl ruthenium dihydride, pyrrolyl ruthenium dihydride and methylpyrrolyl ruthenium dihydride.

Examples of osmium compounds represented by the general formula (III) include benzene osmium dichloride, methylbenzene osmium dichloride, hexamethylbenzene osmium dichloride, (p-cymene)osmium dichloride, methoxybenzene osmium dichloride, ethoxybenzene osmium dichloride, hydroxybenzene osmium dichloride, naphthalene osmium dichloride, methylnaphthalene osmium dichloride, 2-phenoxyethanol osmium dichloride, benzene osmium dibromide, methylbenzene osmium dibromide, hexamethylbenzene osmium dibromide, (p-cymene)osmium dibromide, methoxybenzene osmium dibromide, ethoxybenzene osmium dibromide, hydroxybenzene osmium dibromide, naphthalene osmium dibromide, methylnaphthalene osmium dibromide, 2-phenoxyethanol osmium dibromide, benzene osmium diiodide, methylbenzene osmium diiodide, hexamethylbenzene osmium diiodide, (p-cymene)osmium diiodide, methoxybenzene osmium diiodide, ethoxybenzene osmium diiodide, hydroxybenzene osmium diiodide, naphthalene osmium diiodide, methylnaphthalene osmium diiodide, 2-phenoxyethanol osmium diiodide, benzene osmium difluoride, methylbenzene osmium difluoride, hexamethylbenzene osmium difluoride, (p-cymene)osmium difluoride, methoxybenzene osmium difluoride, ethoxybenzene osmium difluoride, hydroxybenzene osmium difluoride, naphthalene osmium difluoride, methylnaphthalene osmium difluoride, 2-phenoxyethanol osmium difluoride, benzene osmium dihydride, methylbenzene osmium dihydride, hexamethylbenzene osmium dihydride, (p-cymene)osmium dihydride, methoxybenzene osmium dihydride, ethoxybenzene osmium dihydride, hydroxybenzene osmium dihydride, naphthalene osmium dihydride, methylnaphthalene osmium dihydride, 2-phenoxyethanol osmium dihydride, cyclooctatetraene osmium dichloride, norbornadiene osmium dichloride, cyclpentadienyl osmium dichloride, methylcyclopentadienyl osmium dichloride, pentamethylcyclopentadienyl osmium dichloride, pyrrolyl osmium dichloride, methylpyrrolyl osmium dichloride, cyclopentadienyl osmium dibromide, methylcyclopentadienyl osmium dibromide, pentamethylcyclopentadienyl osmium dibromide, pyrrolyl osmium dibromide, methylpyrrolyl osmium dibromide, cyclopentadienyl osmium diiodide, methylcyclopentadienyl osmium diiodide, pentamethylcyclopentadienyl osmium diiodide, pyrrolyl osmium diiodide, methylpyrrolyl osmium diiodide, cyclopentadienyl osmium difluoride, methylcyclopentadienyl osmium difluoride, pentamethylcyclopentadienyl osmium difluoride, pyrrolyl osmium difluoride, methylpyrrolyl osmium difluoride, cyclopentadienyl osmium dihydride, methylcyclopentadienyl osmium dihydride, pentamethylcyclopentadienyl osmium dihydride, pyrrolyl osmium dihydride and methylpyrrolyl osmium dihydride.

Examples of rhodium compounds represented by the general formula (III) include chloro(cyclooctadiene)rhodium, cyclooctadiene(μ-hydroxo)rhodium, cyclooctadiene(μ-methoxo)rhodium, cyclooctadiene(μ-ethoxo)rhodium, cyclooctadiene(μ-isopropoxo)rhodium, fluoro(cyclooctadiene)rhodium, bromo(cyclooctadiene)rhodium, iodo(cyclooctadiene)rhodium, fluoro(norbornadiene)rhodium, chloro(norbornadiene)rhodium, bromo(norbornadiene)rhodium, iodonorbornadiene rhodium, cyclooctadiene(μ-sulfanido)rhodium, chlorobiscyclooctene rhodium, biscyclooctene(μ-hydroxo)rhodium, biscyclooctene(μ-methoxo)rhodium, biscyclooctene(μ-ethoxo)rhodium, biscyclooctene(μ-isopropoxo)rhodium, fluorobiscyclooctene rhodium, bromobiscyclooctene rhodium, iodobiscyclooctene rhodium, chlorobisethylene rhodium, bisethylene(μ-hydroxo)rhodium, bisethylene(μ-methoxo)rhodium, bisethylene(μ-ethoxo)rhodium, bisethylene(μ-isopropoxo)rhodium, fluorobisethylene rhodium, bromobisethylene rhodium, iodobisethylene rhodium, cyclopentadienyl rhodium dichloride, methylcyclopentadienyl rhodium dichloride, pentamethylcyclopentadienyl rhodium dichloride, pyrrolyl rhodium dichloride, methylpyrrolyl rhodium dichloride, cyclopentadienyl rhodium dibromide, methylcyclopentadienyl rhodium dibromide, pentamethylcyclopentadienyl rhodiumdibromide, pyrrolyl rhodium dibromide, methylpyrrolyl rhodium dibromide, cyclopentadienyl rhodium diiodide, methylcyclopentadienyl rhodium diiodide, pentamethylcyclopentadienyl rhodium diiodide, pyrrolyl rhodium diiodide, methylpyrrolyl rhodium diiodide, cyclopentadienyl rhodium difluoride, methylcyclopentadienyl rhodium difluoride, pentamethylcyclopentadienyl rhodium difluoride, pyrrolyl rhodium difluoride, methylpyrrolyl rhodium difluoride, cyclopentadienyl rhodium dihydride, methylcyclopentadienyl rhodium dihydride, pentamethylcyclopentadienyl rhodium dihydride, pyrrolyl rhodium dihydride, methylpyrrolyl rhodium dihydride, acetylacetonato(cyclooctadiene)rhodium, acetylacetonato(biscyclooctene)rhodium, acetylacetonato(bisethylene)rhodium, acetylacetonato(norbornadiene)rhodium, 1,3-diphenyl-1,3-propanedionato(cyclooctadiene)rhodium, 1,3-diphenyl-1,3-propanedionato(biscyclooctene)rhodium, 1,3-diphenyl-1,3-propanedionato(bisethylene)rhodium, 1,3-diphenyl-1,3-propanedionato(norbornadiene)rhodium, 2,2,6,6-tetramethyl-3,5-heptanedionato(cyclooctadiene)rhodium, 2,2,6,6-tetramethyl-3,5-heptanedionato(biscyclooctene)rhodium, 2,2,6,6-tetramethyl-3,5-heptanedionato(bisethylene)rhodium, 2,2,6,6-tetramethyl-3,5-heptanedionato(norbornadiene)rhodium, hexafluoroacetylacetonato(cyclooctadiene)rhodium, hexafluoroacetylacetonato(biscyclooctene)rhodium, hexafluoroacetylacetonato(bisethylene)rhodium and hexafluoroacetylacetonato(norbornadiene)rhodium.

Examples of iridium compounds represented by the general formula (III) include chloro(cyclooctadiene)iridium, cyclooctadiene(μ-hydroxy)iridium, cyclooctadiene(μ-methoxo)iridium, cyclooctadiene(μ-ethoxo)iridium, cyclooctadiene(μ-isopropoxo)iridium, fluoro(cyclooctadiene)iridium, bromo(cyclooctadiene)iridium, iodo(cyclooctadiene)iridium, fluoronorbornadiene iridium, chloronorbornadiene iridium, bromo(norbornadiene)iridium, iodonorbornadiene iridium, cyclooctadiene(μ-sulfanido)iridium, chlorobiscyclooctene iridium, biscyclooctene(μ-hydroxo)iridium dimer, biscyclooctene(μ-methoxo)iridium, biscyclooctene(μ-ethoxo)iridium, biscyclooctene(μ-isopropoxo)iridium, fluorobiscyclooctene iridium, bromobiscyclooctene iridium, iodobiscyclooctene iridium, chlorobisethylene iridium, bisethylene(μ-hydroxo)iridium, bisethylene(μ-methoxo)iridium, bisethylene(μ-ethoxo)iridium, bisethylene(μ-isopropoxo)iridium, fluorobisethylene iridium, bromobisethylene iridium, iodobisethylene iridium, cyclopentadienyl iridium dichloride, methylcyclopentadienyl iridium dichloride, pentamethylcyclopentadienyl iridium dichloride, pyrrolyl iridium dichloride, methylpyrrolyl iridium dichloride, cyclopentadienyl iridium dibromide, methylcyclopentadienyl iridium dibromide, pentamethylcyclopentadienyl iridiumdibromide, pyrrolyl iridium dibromide, methylpyrrolyl iridium dibromide, cyclopentadienyl iridium diiodide, methylcyclopentadienyl iridium diiodide, pentamethylcyclopentadienyl iridium diiodide, pyrrolyl iridium diiodide, methylpyrrolyl iridium diiodide, cyclopentadienyl iridium difluoride, methylcyclopentadienyl iridium difluoride, pentamethylcyclopentadienyl iridium difluoride, pyrrolyl iridium difluoride, methylpyrrolyl iridium difluoride, cyclopentadienyl iridium dihydride, methylcyclopentadienyl iridium dihydride, pentamethylcyclopentadienyl iridium dihydride, pyrrolyl iridium dihydride, methylpyrrolyl iridium dihydride, acetylacetonato(cyclooctadiene)iridium, acetylacetonato(biscyclooctene)iridium, acetylacetonato(bisethylene)iridium, acetylacetonato(norbornadiene)iridium, 1,3-diphenyl-1,3-propanedionato(cyclooctadiene)iridium, 1,3-diphenyl-1,3-propanedionato(biscyclooctene)iridium, 1,3-diphenyl-1,3-propanedionato(bisethylene)iridium, 1,3-diphenyl-1,3-propanedionato(norbornadiene)iridium, 2,2,6,6-tetramethyl-3,5-heptanedionato(cyclooctadiene)iridium, 2,2,6,6-tetramethyl-3,5-heptanedionato(biscyclooctene)iridium, 2,2,6,6-tetramethyl-3,5-heptanedionato(bisethylene)iridium, 2,2,6,6-tetramethyl-3,5-heptanedionato(norbornadiene)iridium, hexafluoroacetylacetonato(cyclooctadiene)iridium, hexafluoroacetylacetonato(biscyclooctene)iridium, hexafluoroacetylacetonato(bisethylene)iridium and hexafluoroacetylacetonato(norbornadiene)iridium.

In the composite, the quantity ratio between the compound (III) and the compound (IIa) or (IIb) is as follows. From the viewpoints of catalytic activity and reaction rate, the quantity of the compound (IIa) or (IIb) is usually 0.01 to 100 mol, preferably 0.1 to 10 mol, more preferably 0.5 to 5 mol, based on 1 mol of the compound (III).

Furthermore, the present invention provides a catalyst containing the metal complex compound (I) and a catalyst containing the composite constituted of the compound (III) and the compound (IIa) or (IIb). Such catalysts have high activity as hydration catalysts particularly in the production of amides from nitriles.

Although there is no limitation on the nitrile compounds to which the catalysts of the present invention can be applied, there can be mentioned, for example, aliphatic nitriles and aromatic nitriles of 1 to 30 carbon atoms, each of which may have a substituent. Examples of the aliphatic nitriles include monovalent aliphatic nitriles, such as acetonitrile, propionitrile and butylonitrile, polyvalent aliphatic nitriles, such as malononitrile, succinonitrile and adiponitrile, and unsaturated aliphatic nitriles, such as acrylonitrile and methacrylonitrile. Examples of the aromatic nitriles include benzonitrile, 3-cyanopyridine and phthalonitrile. The catalysts of the present invention are preferable for use particularly in the production of acryliamide from acrylonitrile.

The catalysts of the present invention may contain a reaction accelerator in addition to the metal complex compound (I) or the composite constituted of the compound (III) and the compound (IIa) or (IIb). The reaction accelerator is, for example, an oxygen-containing compound. As an example of the oxygen-containing compound, an organophosphorus compound corresponding to the compound (IIa) or (IIb), which is thought to function as a further ligand of the metal complex compound, can be given, and such a compound can be selected from diphenylphosphine oxide which may have a substituent, dialkylphosphine oxide which may have a substituent, phosphine oxide having a phenyl group which may have a substituent or an alkyl group which may have a substituent, a phosphorous acid dialkyl ester of 1 to 30 carbon atoms, a phosphorous acid diphenyl ester which may have a substituent and a phosphorous acid ester having a phenyl group which may have a substituent and having an alkyl group which may have a substituent.

Specifically, there can be mentioned diphenylphosphine oxide, di-n-butylphosphineoxide, n-butylphenylphosphineoxide, dimethylphosphine oxide, diethylphosphine oxide, diethyl phosphite, dibutyl phosphite, diisobutyl phosphite, di-t-butyl phosphite, diphenyl phosphite, phenylphosphinic acid, diphenylphosphine sulfide, etc.

As the oxygen-containing compound, a compound containing a hydroxyl group can be further mentioned, and such a compound can be selected from an aliphatic alcohol which may have a substituent, an aromatic alcohol which may have a substituent, an aliphatic carboxylic acid which may have a substituent and an aromatic carboxylic acid which may have a substituent. Specifically, there can be mentioned methanol, ethanol, 2-propanol, n-butanol, t-butanol, n-octanol, phenol, 2-methoxyphenol, 3-methoxyphenol, 4-methoxyphenol, 2-methylphenol, 3-methylphenol, 4-methylphenol, 2-chlorophenol, 2-fluorophenol, 3-fluorophenol, 4-fluorophenol, pentafluorophenol, acetic acid, benzoic acid, etc.

The reaction accelerator can be contained in an amount of 0.1 to 100 mol, based on 1 mol of the metal complex compound (I) or the compound (IIa) or (IIb), and it is preferably contained in an amount of 0.5 to 10 mol, more preferably 1 to 5 mol. If the amount thereof is less than 0.1 mol, there is a disadvantage that the catalytic efficiency is not enhanced. If the amount thereof is more than 100 mol, there are disadvantages from the viewpoints of complicated process for separation from the desired product and economical efficiency.

As the process for producing amides by hydration of nitriles using the catalyst of the present invention, there can be mentioned a process comprising adding the catalyst of the present invention to a mixture of nitriles and water and/or an organic solvent and performing reaction. Water and the organic solvent can be each used alone or can be used as a mixture. The amount of water and/or the organic solvent used herein (amount of water used alone, amount of organic solvent used alone, or amount of mixture of water and organic solvent used) may be 0.1 to 10000 mol based on 1 mol of nitrile group, and the amount thereof is preferably 0.5 to 1000 mol, more preferably 1 to 100 mol. If the amount of water and/or the organic solvent is too small, the yield of amide produced is markedly lowered. Even if the amount thereof is too large, the yield of amide produced is lowered because contact of nitrile with the catalyst is inhibited.

The reaction temperature can be selected from the range of 0° C. to 150° C., and it is preferably 30 to 130° C., more preferably 40 to 120° C. If the reaction temperature is too low, the reaction rate is lowered to bring about an industrial disadvantage. If the reaction temperature is too high, problems such as decomposition of the catalytic component and increase of production cost occur. The reaction time has only to be in the range of 0.1 to 48 hours, and it is preferably 0.1 to 10 hours, more preferably 1 to 5 hours.

The reaction pressure is arbitrary one provided that it is a pressure of such a degree as keeps the reaction system in the liquid phase, and when the reaction proceeds at a temperature of not higher than the boiling point of water, a pressure container is not necessary. When the reaction is carried out in a closed system, the reaction atmosphere is preferably an atmosphere of an inert gas such as nitrogen, argon, helium or carbon dioxide. The reaction can be carried out by a batch process or a continuous process. From the liquid reaction mixture, an amide compound that is a product can be recovered by distillation, crystallization or the like. In the residual liquid given after the recovery of the product (e.g., filtrate given after filtration of the precipitated amide compound), the catalyst is dissolved, and therefore, the liquid can be directly or indirectly circulated and used for the reaction again, or from the liquid the catalyst may be recovered, if desired.

EXAMPLES

The present invention is further described with reference to the following examples, but it should be construed that the present invention is in no way limited to those examples.

Examples 1-1 to 1-12

In a screw-top glass test tube, the following complex A (0.005 mmol Ru), the following ligand a (0.01 mmol), acrylonitrile (67 μL, 1 mmol), a given amount of water and 0.5 mL of a solvent were placed in an argon atmosphere, and the test tube was closed. Then, the test tube was heated at a given temperature for a given period of time. The yield of acrylamide was calculated by a gas chromatograph. The results of the hydration reactions of acrylonitrile are set forth in Table 1-1.

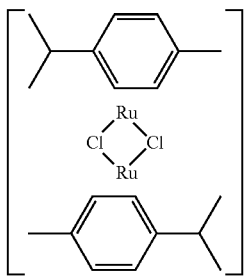

A

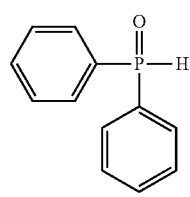

a

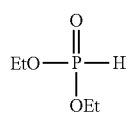

b

TABLE 1-1

Performance of catalyst composed of complex A and ligand a [a]

| Example | Solvent | Amount of water (mmol) | Temperature (°C.) | Reaction time (h) | Yield of acrylamide (%) |
|---|---|---|---|---|---|
| 1-1 | EtOH | 4 | 80 | 3.5 | 72 |
| 1-2 | EtOH | 1 | 80 | 3.5 | 20 |
| 1-3 | MeOH | 4 | 80 | 3.5 | 5 |
| 1-4 | MeOH | 1 | 80 | 3.5 | 2 |
| 1-5 | toluene | 4 | 80 | 3.5 | >99 |
| 1-6 | toluene | 1 | 80 | 3.5 | 6 |
| 1-7 | 1,2-dimethoxyethane | 4 | 80 | 3.5 | 40 |
| 1-8 | 2-propanol | 4 | 80 | 3.5 | >99 |
| 1-9 | 2-propanol | 1 | 80 | 3.5 | 32 |
| 1-10 | 2-propanol | 4 | 80 | 1 | 84 |
| 1-11 | water | amount of solvent | 80 | 3.5 | 23 |
| 1-12 | EtOH | 4 | rt | 24 | 49 |

[a] Amount used: acrylonitrile: 1 mmol, solvent: 0.5 mL, complex A: 0.005 mmol (Ru, 0.5 mol % based on acrylonitrile), ligand a: 0.01 mmol; Experiment was carried out in argon atmosphere.

Examples 1-13 and 1-14

Table 1-2 shows experimental examples which were carried out in the same manner as in Examples 1-1 to 1-12 but in which the catalytic amount (amount of complex A) was increased.

TABLE 1-2

Performance of catalyst composed of complex A and ligand a [a]

| Example | Solvent | Amount of water (mmol) | Temperature (°C.) | Reaction time (h) | Yield of acrylamide (%) |
|---|---|---|---|---|---|
| 1-13 | EtOH | 4 | 80 | 3.5 | >99 |
| 1-14 | EtOH | 4 | rt | 24 | >99 |

[a] Amount used: acrylonitrile: 1 mmol, solvent: 0.5 mL, complex A: 0.05 mmol (Ru, 5 mol % based on acrylonitrile), ligand a: 0.10 mmol; Experiment was carried out in argon atmosphere.

Examples 1-15 to 1-20

Table 1-3 shows experimental examples in which the proportions (molar ratios) of the complex A and the ligand a were changed.

TABLE 1-3

Performance of catalyst comprising complex A and ligand a [a], Study of amount of ligand a

| Example | Amount of ligand a (molar ratio to Ru) | Yield of acrylamide (%) |
|---|---|---|
| 1-15 | 0.5 | 30 |
| 1-16 | 1 | 80 |
| 1-17 [b] | 1 | 39 |
| 1-18 | 2 | 84 |
| 1-19 | 3 | 85 |
| 1-20 | 4 | 83 |

[a] Amount used: acrylonitrile: 1 mmol, solvent: 0.5 mL (2-propanol), complex A: 0.005 mmol (Ru) (0.5 mol % based on acrylonitrile); Experiment was carried out in argon atmosphere at 80° C. for 1 hour.
[b] Solvent: toluene Examples 2-1 to 2-12

In a screw-top glass test tube, the aforesaid complex A (0.05 mmol Ru), the ligand b (0.01 mmol), acrylonitrile (67

μL, 1 mmol), a given amount of water and 0.5 mL of a solvent were placed in an argon atmosphere, and the test tube was closed. Then, the test tube was heated at a given temperature for a given period of time. The yield of acrylamide was calculated by a gas chromatograph. The results of the hydration reactions of acrylonitrile are set forth in Table 2.

TABLE 2

Performance of catalyst composed of complex A and ligand b [a]

| Example | Solvent | Amount of water (mmol) | Temperature (° C.) | Reaction time (h) | Yield of acrylamide (%) |
|---|---|---|---|---|---|
| 2-1 | EtOH | 4 | 80 | 3.5 | 32 |
| 2-2 | EtOH | 1 | 80 | 3.5 | 16 |
| 2-3 | MeOH | 4 | 80 | 3.5 | 9 |
| 2-4 | MeOH | 1 | 80 | 3.5 | 6 |
| 2-5 | toluene | 4 | 80 | 3.5 | 3 |
| 2-6 | toluene | 1 | 80 | 3.5 | 3 |
| 2-7 | 1,2-dimethoxyethane | 4 | 80 | 3.5 | 40 |
| 2-8 | THF | 4 | 80 | 3.5 | 56 |
| 2-9 | 2-propanol | 4 | 80 | 3.5 | 77 |
| 2-10 | 2-propanol | 1 | 80 | 3.5 | 19 |
| 2-11 | water | amount of solvent | 80 | 3.5 | 8 |
| 2-12 | EtOH | 4 | rt | 24 | 58 |

[a] Amount used: acrylonitrile: 1 mmol, solvent: 0.5 mL, complex A: 0.005 mmol (Ru, 0.5 mol % based on acrylonitrile), ligand b: 0.01 mmol; Experiment was carried out in argon atmosphere.

Examples 3-1 to 3-8

Synthesis of complex B: In a Schlenk flask, a (p-cymene) ruthenium dichloride dimer A (0.50 g, 0.82 mmol) and diphenylphosphine oxide (0.33 g, 1.64 mmol) were placed in an argon atmosphere. By the use of a syringe, 40 mL of toluene having been degassed and dehydrated was added, and the flask was stoppered, followed by stirring at room temperature for 1 hour. After the stirring was completed, the solvent was distilled off under reduced pressure to obtain the following complex B as a red brown powder (0.83 g, 1.64 mmol).

NMR Data of Complex B $^1$H NMR (C$_6$D$_6$) δ 0.82 (d, J=6.8 Hz, 6H), 1.69 (s, 3H), 2.50 (quin, J=6.8 Hz, 1H), 4.85-4.91 (m, 4H), 7.08-7.19 (m, 6H), 7.75-7.81 (m, 4H). $^{31}$P{$^1$H} NMR (C$_6$D$_6$) δ 105.4 (s).

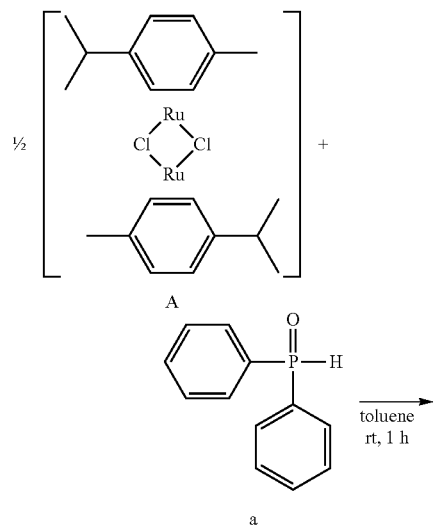

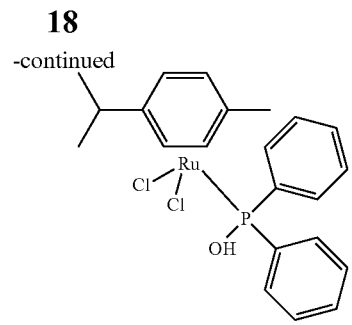

B
>99%

In a screw-top glass test tube, the complex B (0.005 mmol Ru), acrylonitrile (67 μL, 1 mmol), a given amount of water and 0.5 mL of a solvent were placed in an argon atmosphere, and the test tube was closed. Then, the test tube was heated at 80° C. for a given period of time. The yield of acrylamide was calculated by a gas chromatograph. The results of the hydration reactions of acrylonitrile are set forth in Table 3.

TABLE 3

Catalytic performance of complex B [a]

| Example | Solvent | Amount of water (mmol) | Temperature (° C.) | Reaction time (h) | Yield of acrylamide (%) |
|---|---|---|---|---|---|
| 3-1 | 2-propanol | 4 | 80 | 3.5 | >99 |
| 3-2 | water | amount of solvent | 80 | 3.5 | 54 |
| 3-3 | acrylonitrile | 1 | 80 | 3.5 | 69 |
| 3-4 [b] | 2-propanol | 4 | 80 | 3.5 | >99 |
| 3-5 [c] | water | 8 | 80 | 3.5 | >99 |
| 3-6 | toluene | 4 | 80 | 1 | 43 |
| 3-7 | 2-propanol | 4 | 80 | 1 | 81 |
| 3-8 | 2-propanol | 1 | 80 | 1 | 26 |

[a] Amount used: acrylonitrile: 1 mmol, solvent: 0.5 mL, complex B: 0.005 mmol (0.5 mol % based on acrylonitrile); Experiment was carried out in argon atmosphere.
[b] Experiment was carried out in air.
[c] Experiment was carried out under the conditions set so that the product might become 50% acrylamide aqueous solution.

Examples 4-1 to 4-7

Next, experiments in which a reaction accelerator was added to the catalyst system of the complex B were carried out, and the results are set forth in Table 4. In a screw-top glass test tube, the complex B (0.005 mmol Ru), a given amount of an additive, acrylonitrile (67 μL, 1 mmol), water (72 μL, 4 mmol) and 0.5 mL of toluene as a solvent were placed in an argon atmosphere, and the test tube was closed. Then, the test tube was heated at 80° C. for 1 hour. The yield of acrylamide was calculated by a gas chromatograph.

TABLE 4

Catalytic performance of system of complex B mixed with reaction accelerator [a]

| Example | Additive | Amount of additive (mmol) | Yield of acrylamide (%) |
|---|---|---|---|
| 4-1 | None | 0 | 25 |
| 4-2 | diethyl phosphite (ligand b) | 0.10 | 64 |

TABLE 4-continued

Catalytic performance of system of complex B mixed with reaction accelerator [a]

| Example | Additive | Amount of additive (mmol) | Yield of acrylamide (%) |
|---|---|---|---|
| 4-3 | isobutyl phosphite | 0.10 | 94 |
| 4-4 | diphenylphosphine oxide (ligand a) | 0.10 | 98 |
| 4-5 | dibutylphosphine oxide | 0.10 | >99 |
| 4-6 | dibutylphosphine oxide | 0.015 | 54 |
| 4-7 | phenylphosphinic acid | 0.10 | >99 |

[a] Amount used: acrylonitrile: 1 mmol, water: 4 mmol, solvent (toluene): 0.5 mL, complex B: 0.005 mmol (0.5 mol % based on acrylonitrile); Reaction temperature: 80° C., Reaction time: 1 hour; Experiment was carried out in argon atmosphere.

Examples 5-1 to 5-9

Synthesis of complex C: In a Schlenk flask, a benzene ruthenium dichloride dimer (0.50 g, 1.00 mmol) and diphenylphosphine oxide (0.40 g, 2.00 mmol) were placed in an argon atmosphere. By the use of a syringe, 30 mL of degassed and dehydrated dichloromethane was added, and the flask was stoppered, followed by stirring at room temperature for 1 hour. After the stirring was completed, the solvent was distilled off under reduced pressure to obtain the following complex C as a red brown powder (0.80 g, 0.88 mmol). The complex C* was synthesized in the same manner as above, except that the solvent was changed to acetonitrile.

NMR Data of Complex C $^1$H NMR ($C_6D_6$) δ 4.40 (d, 6H), 7.08-7.19 (m, 6H), 7.75-7.81 (m, 4H). $^{31}$P{$^1$H} NMR ($C_6D_6$) δ 101.1 (s).

Synthesis of complex D: In a Schlenk flask, a hexamethylbenzene ruthenium dichloride dimer (0.67 g, 1.00 mmol) and diphenylphosphine oxide (0.40 g, 2.00 mmol) were placed in an argon atmosphere. By the use of a syringe, 40 mL of degassed and dehydrated toluene was added, and the flask was stoppered, followed by stirring at room temperature for 1 hour. After the stirring was completed, the solvent was distilled off under reduced pressure to obtain the following complex D as a red brown powder (1.07 g, 1.00 mmol).

NMR Data of Complex D $^1$H NMR ($C_6D_6$) δ 1.55 (m, 18H), 7.00-7.19 (m, 6H), 7.75-7.90 (m, 4H). $^{31}$P{$^1$H} NMR ($C_6D_6$) δ 115.6 (s).

Synthesis of complex E: In a Schlenk flask, a (p-cymene) ruthenium dichloride dimer (0.31 g, 0.50 mmol) and di-n-butylphosphine oxide (0.16 g, 1.00 mmol) were placed in an argon atmosphere. By the use of a syringe, 40 mL of degassed and dehydrated toluene was added, and the flask was stoppered, followed by stirring at room temperature for 1 hour. After the stirring was completed, the solvent was distilled off under reduced pressure to obtain the following complex E as a red brown powder (0.46 g, 1.00 mmol).

$^1$H NMR ($C_6D_6$) δ 0.92 (t, J=7.3 Hz, 6H), 1.08 (d, J=7.0 Hz, 6H), 1.81, 1.88 (s, 3H), 1.10=2.25 (m, 12H), 4.85-5.13 (m, 4H). $^{31}$P{$^1$H} NMR ($C_6D_6$) δ 121.4 (s).

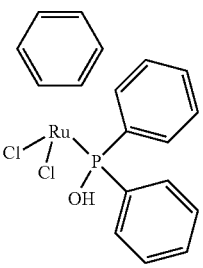

C

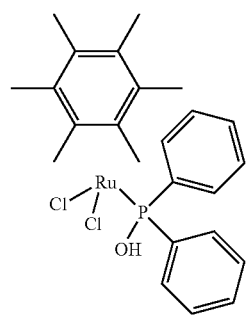

D

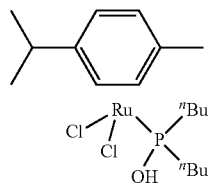

E

Experiments with the catalyst systems using the complexes C, D and E were carried out, and the results are set forth in Table 5. In a screw-top glass test tube, a given complex (0.005 mmol Ru), acrylonitrile (67 μL, 1 mmol), a given amount of water and 0.5 mL of a solvent were placed in an argon atmosphere, and the test tube was closed. Then, the test tube was heated at 80° C. for a given period of time. The yield of acrylamide was calculated by a gas chromatograph.

TABLE 5

Catalytic performance of complexes C, D and E[a]

| Example | Complex | Solvent | Amount of water (mmol) | Temperature (° C.) | Reaction time (h) | Yield of acrylamide (%) |
|---|---|---|---|---|---|---|
| 5-1 | C | toluene | 4 | 80 | 1 | 38 |
| 5-2 | C | 2-propanol | 4 | 80 | 1 | 66 |
| 5-3 | D | water | amount of solvent | 80 | 3.5 | 95 |
| 5-4[b] | D | water | amount of solvent | 80 | 3.5 | 88 |
| 5-5 | D | toluene | 4 | 80 | 1 | 1 |
| 5-6 | D | 2-propanol | 4 | 80 | 1 | 5 |
| 5-7 | E | toluene | 4 | 80 | 1 | 27 |
| 5-8 | E | 2-propanol | 4 | 80 | 1 | 9 |
| 5-9 | C*[c] | 2-propanol | 4 | 80 | 3.5 | 76 |

[a] Amount used: acrylonitrile: 1 mmol, solvent: 0.5 mL, ruthenium complex: 0.005 mmol (0.5 mol % based on acrylonitrile); Experiment was carried out in argon atmosphere.
[b] Experiment was carried out in air.
[c] The solvents in syntheses of complexes were different (C: dichloromethane, C*: acetonitrile).

Examples 6-1 to 6-4

The results obtained by adding a reaction accelerator to the complex B are set forth in Table 6. In a screw-top glass test tube, the complex B (0.005 mmol Ru), a given amount of an additive, acrylonitrile (67 μL, 1 mmol), water (72 μL, 4 mmol) and 0.5 mL of toluene as a solvent were placed in an argon atmosphere, and the test tube was closed. Then, the test tube was heated at 80° C. for 1 hour. The yield of acrylamide was calculated by a gas chromatograph.

TABLE 6

Catalytic performance of system of complex B mixed with reaction accelerator [a]

| Example | Additive | Amount of additive (mmol) | Yield of acrylamide (%) |
|---|---|---|---|
| 6-1 | none | 0 | 25 |
| 6-2 | phenol | 0.10 | 18 |
| 6-3 | pentafluorophenol | 0.10 | 86 |
| 6-4 | benzoic acid | 0.10 | 47 |

[a] Amount used: acrylonitrile: 1 mmol, water: 4 mmol, solvent (toluene): 0.5 mL, complex B: 0.005 mmol (0.5 mol % based on acrylonitrile)

Examples 7-1 to 7-11

Experimental examples of hydration reactions of acrylonitrile using a catalyst composed of the complex A and the following ligand c, d, e, f, g or h are set forth in Table 7. In a screw-top glass test tube, the complex A (0.005 mmol Ru), a given amount of a ligand, acrylonitrile (67 μL, 1 mmol), water (72 μL, 4 mmol) and 0.5 mL of a given solvent were placed in an argon atmosphere, and the test tube was closed. Then, the test tube was heated at 80° C. for a given period of time. The yield of acrylamide was calculated by a gas chromatograph.

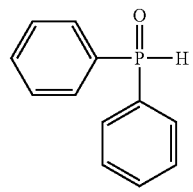

a

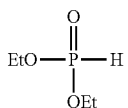

b

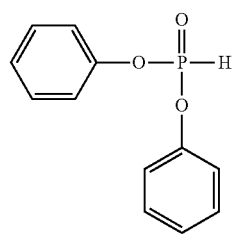

c

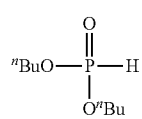

d

-continued

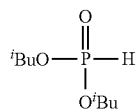

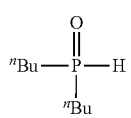

e

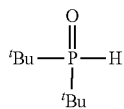 g f

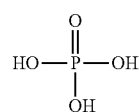 h

TABLE 7

Performance of catalyst composed of complex A and any one of ligands c to h[a]

| Example | Ligand | Solvent | Amount of ligand (molar ratio to Ru) | Temperature (°C.) | Reaction time (h) | Yield of acrylamide (%) |
|---|---|---|---|---|---|---|
| ref. (1-10) | a | 2-propanol | 2 | 80 | 1 | 84 |
| 7-1 | f | 2-propanol | 2 | 80 | 1 | 56 |
| 7-2 | f | 2-propanol | 2 | 80 | 3.5 | >99 |
| 7-3 | f | 2-propanol | 1 | 80 | 1 | 3 |
| 7-4 | f | toluene | 1 | 80 | 1 | 61 |
| 7-5 | g | toluene | 1 | 80 | 1 | 0 |
| 7-6 | g | 2-propanol | 1 | 80 | 1 | 0 |
| 7-7 | h | toluene | 100 | 80 | 3.5 | 0 |
| 7-8 | h | 2-propanol | 100 | 80 | 3.5 | 1 |
| ref. (2-1) | b | EtOH | 2 | 80 | 3.5 | 32 |
| 7-9 | c | EtOH | 2 | 80 | 3.5 | 48 |
| 7-10 | d | EtOH | 2 | 80 | 3.5 | 30 |
| 7-11 | e | EtOH | 2 | 80 | 3.5 | 30 |

[a] Amount used: acrylonitrile: 1 mmol, water: 4 mmol, solvent: 0.5 mL, complex A: 0.005 mmol (Ru, 0.5 mol % based on acrylonitrile); Experiment was carried out in argon atmosphere.

Examples 8-1 to 8-23

Experiments of hydration reactions of acrylonitrile using the following complexes F, G, H and I were carried out, and the results are set forth in Table 8. In a screw-top glass test tube, the complex (0.005 mmol Ru), a given amount of a ligand, acrylonitrile (67 μL, 1 mmol), water (72 μL, 4 mmol) and 0.5 mL of a given solvent were placed in an argon atmosphere, and the test tube was closed. Then, the test tube was heated at a given temperature for a given period of time. The yield of acrylamide was calculated by a gas chromatograph.

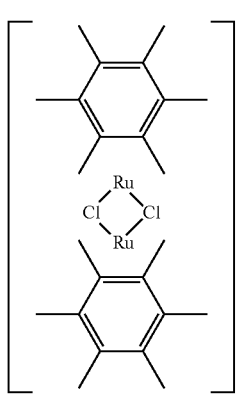

F

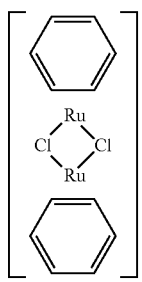

G

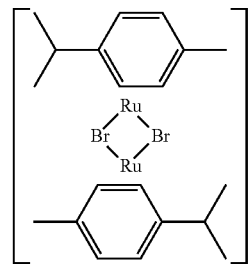

H

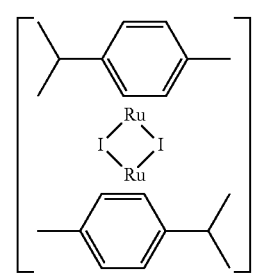

I

TABLE 8

Performance of catalyst comprising any one of complexes E to H and any one of ligands a to e[a)]

| Example | Complex | Ligand | Solvent | Amount of ligand (molar ratio to Ru) | Temperature (° C.) | Reaction time (h) | Yield of acrylamide (%) |
|---|---|---|---|---|---|---|---|
| 8-1 | F[b)] | b | 2-propanol | 2 | 80 | 3.5 | 19 |
| 8-2 | F[b)] | b | water | 2 | 80 | 3.5 | 7 |
| 8-3 | F | a | 2-propanol | 2 | 80 | 3.5 | 15 |
| 8-4 | F | a | water | 2 | 80 | 3.5 | 30 |
| 8-5 | G[b)] | b | 2-propanol | 2 | 80 | 3.5 | 34 |
| 8-6 | G[b)] | b | water | 2 | 80 | 3.5 | 3 |
| 8-7 | G[b)] | B | THF | 2 | 80 | 3.5 | 27 |
| 8-8 | G | A | 2-propanol | 2 | 80 | 3.5 | >99 |
| 8-9 | G | A | 2-propanol | 2 | 80 | 1 | 84 |
| 8-10 | G | a | 2-propanol | 1 | 80 | 1 | 71 |
| 8-11 | G | a | 2-propanol | 2 | 25 | 24 | 41 |
| 8-12 | G | a | 2-propanol | 2 | 40 | 3.5 | 25 |
| 8-13 | G | a | 2-propanol | 2 | 120 | 0.1 | 30 |
| 8-14 | G | a | toluene | 2 | 80 | 3.5 | 55 |
| 8-15 | H | a | 2-propanol | 2 | 80 | 3.5 | >99 |
| 8-16 | H | a | EtOH | 2 | 80 | 3.5 | 74 |
| 8-17 | H[b)] | c | EtOH | 2 | 80 | 3.5 | 57 |
| 8-18 | H | a | toluene | 1 | 80 | 1 | 25 |
| 8-19 | H | a | 2-propanol | 1 | 80 | 1 | 74 |
| 8-20 | I | a | 2-propanol | 2 | 80 | 3.5 | 68 |
| 8-21 | I | a | EtOH | 2 | 80 | 3.5 | 61 |

TABLE 8-continued

Performance of catalyst comprising any one of complexes E to H and any one of ligands a to e [a]

| Example | Complex | Ligand | Solvent | Amount of ligand (molar ratio to Ru) | Temperature (°C.) | Reaction time (h) | Yield of acrylamide (%) |
|---|---|---|---|---|---|---|---|
| 8-22 | I | a | toluene | 1 | 80 | 1 | 9 |
| 8-23 | I [b] | c | EtOH | 2 | 80 | 3.5 | 34 |

[a] Amount used: acrylonitrile: 1 mmol, water: 4 mmol, solvent: 0.5 mL, complex A: 0.005 mmol (Ru, 0.5 mol % based on acrylonitrile)
[b] Amount used: complex: 0.05 mmol (in terms of Ru, 5 mol % based on acrylonitrile)

Examples 9-1 to 9-8

The results obtained by carrying out catalytic hydration reactions of various nitriles using the complex B are set forth in Table 9. In a screw-top glass test tube, the complex A (0.005 mmol Ru), a given amount of a ligand, acrylonitrile (67 μL, 1 mmol), water (72 μL, 4 mmol) and 0.5 mL of a given solvent were placed in an argon atmosphere, and the test tube was closed. Then, the test tube was heated at 80° C. for a given period of time. The yield of acrylamide was calculated by a gas chromatograph.

TABLE 9

Hydration reaction of nitriles by complex B [a]

| Example | Nitrile | Solvent | Temperature | Yield of amide (%) |
|---|---|---|---|---|
| 9-1 | benzonitrile | EtOH | 80 | >99 |
| 9-2 | octylnitrile | EtOH | 80 | 80 |
| 9-3 | 3-cyanopyridine | EtOH | 80 | >99 |
| 9-4 | methacrylonitrile | EtOH | 80 | >99 |
| 9-5 [c] | polyacrylonitrile | i-PrOH | 40 | b) |
| 9-6 [c] | polyacrylonitrile | i-PrOH | 80 | b) |
| 9-7 [c] | polyacrylonitrile | EtOH | 40 | b) |
| 9-8 [c] | polyacrylonitrile | EtOH | 80 | b) |

[a] Amount used: nitrile: 1 mmol, water: 4 mmol, solvent: 0.5 mL, catalyst: 0.005 mmol metal (0.5 mol % based on nitrile); Reaction temperature: 80° C., Reaction time: 3.5 hours; Experiment was carried out in argon atmosphere.
b) Infrared absorption spectrum (nujol/NaCl) of reaction product was measured, and absorption derived from amido group was confirmed at 1690 cm$^{-1}$ (FIG. 1).
[c] Reaction time: 24 hours Examples 10-1 to 10-67

Examples of hydration reactions of acrylonitrile using a metal complex catalyst containing iridium or rhodium are set forth in Table 10. In a screw-top glass test tube, the complex (0.005 mmol in terms of metal), a given amount of a ligand, acrylonitrile (67 μL, 1 mmol), water (72 μL, 4 mmol) and 0.5 mL of a given solvent were placed in an argon atmosphere, and the test tube was closed. Then, the test tube was heated at 80° C. for a given period of time. The yield of acrylamide was calculated by a gas chromatograph.

TABLE 10

Catalytic activity of metal complex catalyst system [a]

| Example | Complex | Ligand | Solvent | Reaction time (h) | Yield of acrylamide (%) |
|---|---|---|---|---|---|
| 10-1 | [Ir(OH)(cod)]$_2$ | diphenylphosphine oxide (ligand a) | 1,2-dimethoxyethane | 3.5 | >99 |
| 10-2 | [Ir(OH)(cod)]$_2$ | diphenylphosphine oxide (ligand a) | 1,2-dimethoxyethane | 1 | 8 |
| 10-3 | [Ir(OH)(cod)]$_2$ | diphenylphosphine oxide (ligand a) | THF | 3.5 | 75 |
| 10-4 | [Ir(OH)(cod)]$_2$ | diphenylphosphine oxide (ligand a) | 2-propanol | 3.5 | 50 |
| 10-5 | [Ir(OH)(cod)]$_2$ | diphenylphosphine oxide (ligand a) | toluene | 3.5 | 1 |
| 10-6 | [Ir(OH)(cod)]$_2$ | diphenylphosphine oxide (ligand a) | MeOH | 3.5 | 6 |
| 10-7 | [Ir(OH)(cod)]$_2$ | diphenylphosphine oxide (ligand a) | EtOH | 3.5 | 4 |
| 10-8 [b] | [Ir(OH)(cod)]$_2$ | diphenylphosphine oxide (ligand a) | 1,2-dimethoxyethane | 1 | 72 |
| 10-9 [c] | [Ir(OH)(cod)]$_2$ | diphenylphosphine oxide (ligand a) | 1,2-dimethoxyethane | 3.5 | 22 |
| 10-10 [d] | [Ir(OH)(cod)]$_2$ | diphenyl phosphite | THF | 3.5 | 34 |
| 10-11 [c][d] | [Ir(OH)(cod)]$_2$ | diphenyl phosphite | THF | 3.5 | 19 |
| 10-12 [d] | [Ir(OH)(cod)]$_2$ | diphenyl phosphite | 2-propanol | 3.5 | 32 |
| 10-13 [d] | [Ir(OH)(cod)]$_2$ | diphenyl phosphite | 1,2-dimethoxyethane | 3.5 | 29 |
| 10-14 [d] | [Ir(OH)(cod)]$_2$ | diphenyl phosphite | toluene | 3.5 | 28 |
| 10-15 [d] | [Ir(OH)(cod)]$_2$ | diphenyl phosphite | MeOH | 3.5 | 13 |
| 10-16 [d] | [Ir(OH)(cod)]$_2$ | diphenyl phosphite | EtOH | 3.5 | 21 |
| 10-17 [d] | [Ir(OH)(cod)]$_2$ | diethyl phosphite | EtOH | 3.5 | 6 |

TABLE 10-continued

Catalytic activity of metal complex catalyst system [a]

| Example | Complex | Ligand | Solvent | Reaction time (h) | Yield of acrylamide (%) |
|---|---|---|---|---|---|
| 10-18 [d] | [Ir(OH)(cod)]$_2$ | diethyl phosphite | MeOH | 3.5 | 3 |
| 10-19 [d] | [Ir(OH)(cod)]$_2$ | diethyl phosphite | toluene | 3.5 | 4 |
| 10-20 [d] | [Ir(OH)(cod)]$_2$ | diethyl phosphite | 1,2-dimethoxyethane | 3.5 | 4 |
| 10-21 [d] | [Ir(OH)(cod)]$_2$ | diethyl phosphite | THF | 3.5 | 8 |
| 10-22 [c) d)] | [Ir(OH)(cod)]$_2$ | diethyl phosphite | THF | 3.5 | 3 |
| 10-23 [d] | [Ir(OH)(cod)]$_2$ | diethyl phosphite | 2-propanol | 3.5 | 4 |
| 10-24 | [Ir(Cl)(coe)]$_2$ | diphenylphosphine oxide (ligand a) | 2-propanol | 3.5 | 62 |
| 10-25 | [Ir(Cl)(coe)]$_2$ | diphenylphosphine oxide (ligand a) | EtOH | 3.5 | 37 |
| 10-26 [d] | [Ir(Cl)(coe)]$_2$ | diethyl phosphite | EtOH | 3.5 | 3 |
| 10-27 [d] | [Ir(Cl)(coe)]$_2$ | diphenyl phosphite | EtOH | 3.5 | 3 |
| 10-28 [e] | [Ir(O$^i$Pr)(cod)]$_2$ | diethyl phosphite | MeOH | 3.5 | 1 |
| 10-29 [e] | [Ir(O$^i$Pr)(cod)]$_2$ | diethyl phosphite | toluene | 3.5 | 6 |
| 10-30 [e] | [Ir(O$^i$Pr)(cod)]$_2$ | diethyl phosphite | 1,2-dimethoxyethane | 3.5 | 4 |
| 10-31 [e] | [Ir(O$^i$Pr)(cod)]$_2$ | diethyl phosphite | THF | 3.5 | 5 |
| 10-32 [e] | [Ir(O$^i$Pr)(cod)]$_2$ | diethyl phosphite | 2-propanol | 3.5 | 3 |
| 10-33 [f] | [Ir(O$^i$Pr)(cod)]$_2$ | diphenylphosphine oxide (ligand a) | EtOH | 3.5 | 9 |
| 10-34 [f] | [Ir(O$^i$Pr)(cod)]$_2$ | diphenylphosphine oxide (ligand a) | MeOH | 3.5 | 56 |
| 10-35 [f] | [Ir(O$^1$Pr)(cod)]$_2$ | diphenylphosphine oxide (ligand a) | toluene | 3.5 | 43 |
| 10-36 [f) c)] | [Ir(O$^i$Pr)(cod)]$_2$ | diphenylphosphine oxide (ligand a) | toluene | 3.5 | 36 |
| 10-36 [f) g)] | [Ir(O$^i$Pr)(cod)]$_2$ | diphenylphosphine oxide (ligand a) | toluene | 3.5 | 74 |
| 10-37 [f] | [Ir(O$^1$Pr)(cod)]$_2$ | diphenylphosphine oxide (ligand a) | 1,2-dimethoxyethane | 3.5 | 66 |
| 10-38 [f] | [Ir(O$^i$Pr)(cod)]$_2$ | diphenylphosphine oxide (ligand a) | THF | 3.5 | 68 |
| 10-39 | [Ir(O$^i$Pr)(cod)]$_2$ | diphenylphosphine oxide (ligand a) | 2-propanol | 3.5 | 48 |
| 10-40 [e] | [Ir(O$^i$Pr)(cod)]$_2$ | diphenyl phosphite | 2-propanol | 3.5 | 14 |
| 10-41 | [Ir(acac)(cod)]$_2$ | diphenylphosphine oxide (ligand a) | 2-propanol | 3.5 | 11 |
| 10-42 [d] | [Cp*IrCl$_2$]$_2$ | diethyl phosphite | EtOH | 3.5 | 19 |
| 10-43 [d] | [Cp*IrCl$_2$]$_2$ | diethyl phosphite | MeOH | 3.5 | 9 |
| 10-44 [d] | [Cp*IrCl$_2$]$_2$ | diethyl phosphite | 1,2-dimethoxyethane | 3.5 | 2 |
| 10-45 [d] | [Cp*IrCl$_2$]$_2$ | diethyl phosphite | THF | 3.5 | 4 |
| 10-46 [d] | [Cp*IrCl$_2$]$_2$ | diethyl phosphite | 2-propanol | 3.5 | 24 |
| 10-47 [d) c)] | [Cp*IrCl$_2$]$_2$ | diethyl phosphite | 2-propanol | 3.5 | 4 |
| 10-48 | [Cp*IrCl$_2$]$_2$ | diphenylphosphine oxide (ligand a) | EtOH | 3.5 | 22 |
| 10-49 | [Cp*IrCl$_2$]$_2$ | diphenylphosphine oxide (ligand a) | MeOH | 3.5 | 6 |
| 10-50 | [Cp*IrCl$_2$]$_2$ | diphenylphosphine oxide (ligand a) | toluene | 3.5 | 22 |
| 10-51 | [Cp*IrCl$_2$]$_2$ | diphenylphosphine oxide (ligand a) | 1,2-dimethoxyethane | 3.5 | 4 |
| 10-52 | [Cp*IrCl$_2$]$_2$ | diphenylphosphine oxide (ligand a) | THF | 3.5 | 25 |
| 10-52 | [Cp*IrCl$_2$]$_2$ | diphenylphosphine oxide (ligand a) | 2-propanol | 3.5 | 31 |
| 10-53 [c] | [Cp*IrCl$_2$]$_2$ | diphenylphosphine oxide (ligand a) | 2-propanol | 3.5 | 2 |
| 10-54 [d] | [Rh(Cl)(cod)]$_2$ | diethyl phosphite | EtOH | 3.5 | 5 |
| 10-55 [d] | [Rh(Cl)(cod)]$_2$ | diethyl phosphite | MeOH | 3.5 | 3 |
| 10-56 [d] | [Rh(Cl)(cod)]$_2$ | diethyl phosphite | toluene | 3.5 | 4 |
| 10-57 [d] | [Rh(Cl)(cod)]$_2$ | diethyl phosphite | 1,2-dimethoxyethane | 3.5 | 3 |
| 10-58 [d] | [Rh(Cl)(cod)]$_2$ | diethyl phosphite | THF | 3.5 | 2 |
| 10-59 [d] | [Rh(Cl)(cod)]$_2$ | diethyl phosphite | 2-propanol | 3.5 | 5 |
| 10-60 | [Rh(Cl)(cod)]$_2$ | diphenylphosphine oxide (ligand a) | EtOH | 3.5 | 3 |
| 10-61 | [Rh(Cl)(cod)]$_2$ | phenylphosphinic acid | EtOH | 3.5 | 4 |
| 10-62 | [Rh(OH)(cod)]$_2$ | diethyl phosphite | EtOH | 3.5 | 6 |
| 10-63 | [Rh(OH)(cod)]$_2$ | diethyl phosphite | MeOH | 3.5 | 14 |
| 10-64 | [Rh(OH)(cod)]$_2$ | diethyl phosphite | toluene | 3.5 | 1 |
| 10-65 | [Rh(OH)(cod)]$_2$ | diethyl phosphite | 1,2-dimethoxyethane | 3.5 | 3 |

TABLE 10-continued

Catalytic activity of metal complex catalyst system [a]

| Example | Complex | Ligand | Solvent | Reaction time (h) | Yield of acrylamide (%) |
|---|---|---|---|---|---|
| 10-66 | [Rh(OH)(cod)]$_2$ | diethyl phosphite | THF | 3.5 | 2 |
| 10-67 | [Rh(OH)(cod)]$_2$ | diethyl phosphite | 2-propanol | 3.5 | 5 |

[a] Amount used: acrylonitrile: 1 mmol, water: 4 mmol, solvent 0.5 mL, catalyst: 0.005 mmol in terms of metal (0.5 mol % based on acrylonitrile), ligand: 0.010 mmol; Experiment was carried out in argon atmosphere at reaction temperature of 80° C.
[b] Amount used: ligand: 0.015 mmol
[c] Amount used: water: 1.0 mmol,
[d] Amount used: catalyst: 0.05 mmol in terms of metal (5 mol % based on acrylonitrile), ligand: 0.10 mmol,
[e] Amount used: catalyst: 0.025 mmol in terms of metal (2.5 mol % based on acrylonitrile), ligand: 0.075 mmol,
[f] Amount used: catalyst: 0.005 mmol in terms of metal (0.5 mol % based on acrylonitrile), ligand: 0.015 mmol,
[g] Experiment was carried out in air.
cod: 1,5-cyclooctadiene,
coe: cyclooctene,
acac: acetylacetonato group,
Cp*: pentamethylcyclopentadienyl group Examples 11-1 to 11-4 and Comparative Examples 11-1 to 11-3

Experiments for comparison with the catalytic activity of a prior art literature (non patent literature 2, Green Chemistry 12, 790 (2010)) were carried out. The complex 1af described in the non patent literature 2 was synthesized (NMR data are also set forth below because there is no description of the synthesis method in the non patent literature 2). Using the raw material described in the non patent literature 2, the following experiment was carried out.

In a Schlenk flask, a (p-cymene) ruthenium dichloride dimer A (0.306 g, 0.50 mmol) and ethoxy(diphenyl)phosphine oxide (0.230 g, 1.00 mmol) were placed in an argon atmosphere. By the use of a syringe, 10 mL of toluene having been degassed and dehydrated was added, and the flask was stoppered, followed by stirring for 1 hour at room temperature. After the stirring was completed, the solvent was distilled off under reduced pressure to obtain the complex 1af as a red brown powder (0.530 g, 1.0 mmol).

NMR Data of Complex 1af $^1$H NMR (C$_6$D$_6$) δ0.96 (d, J=8.0 Hz, 6H), 1.03 (t, J=7.2 Hz, 3H), 1.64 (s, 3H), 2.74 (q, J=6.8 Hz, 1H), 3.96 (q, J=5.6 Hz, 4H), 4.88-4.97 (m, 4H), 7.02-7.11 (m, 6H), 8.21-8.27 (m, 4H).

$^{31}$P{$^1$H} (C$_6$D$_6$) δ109 (s).

TABLE 11

Performance of ruthenium-based catalyst [a]

| Example, Comparative Example | Complex | Additive | Solvent | Nitrile | Temperature (° C.) | Reaction time (h) | Yield of amide (%) |
|---|---|---|---|---|---|---|---|
| Ex. 11-1 | B | none | water | benzo nitrile | 100 | 2 | 98 |
| Ex. 11-2 | B | TritonX 114 | water | butyro nitrile | 100 | 2 | 84 |
| Ex. 11-3 | B | TritonX 114 | water | butyro nitrile | 100 | 7 | 98 |
| Ex. 11-4 | B | TritonX 114 | EtOH | benzo nitrile | 80 | 3.5 | >99 |
| Comp. Ex. 11-1 | 1af[b] | none | water | benzo nitrile | 100 | 2 | 5 |
| Comp. Ex. 11-2 | 1af[b] | none | EtOH | benzo nitrile | 80 | 3.5 | 19 |
| Comp. Ex. 11-3 | 1af[b] | TritonX 114 | water | butyro nitrile | 100 | 7 | 15 |
| Comp. Ex. 11-4 | 1af[b] | none | 2-propanol | acrylo nitrile | 80 | 3.5 | 0 |

[a] Amount used: nitriles: 0.075 mmol, complex: 0.00375 mmol, water: 4 mmol, solvent: 0.5 mL, additive: 0.075 mmol; Experiment was carried out in argon atmosphere.
[b] Compound 1af described in Green Chemistry 12, 790(2010)

When Examples 11-1 to 11-4 are compared with Comparative Examples 11-1 to 11-3, it can be seen that the experiments of Examples 11-1 to 11-4 differed from those of the comparative examples in having extremely remarkable effects as compared with the experiments using the complex 1af described in the non patent literature 2. When Example 1-8 and Example 3-1 are compared with Comparative Example 11-4, the experiments of Example 1-8 and Example 3-1 differed from the experiment of the comparative example in having extremely remarkable effects as compared with the experiment using the complex 1af described in the non patent literature 2.

Examples 12-1 to 12-9

Experiments of hydration reactions of acrylonitrile using the following complexes J, K and L were carried out. The results are set forth in Table 12. In a screw-top glass test tube, the complex (0.005 mmol in terms of metal), a given amount of a ligand, acrylonitrile (67 μL, 1 mmol), water (72 μL, 4 mmol) and 0.5 mL of a given solvent were placed in an argon atmosphere, and the test tube was closed. Then, the test tube was heated at 80 degrees for 3.5 hours. The yield of acrylamide was calculated by a gas chromatograph.

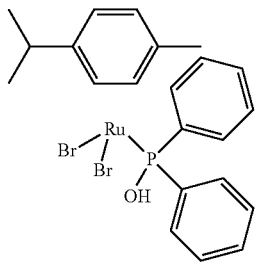

J

K

L

NMR Data of Complex J
$^1$H NMR (C$_6$D$_6$) δ0.84 (d, J=7.2 Hz, 6H), 1.76 (s, 3H), 2.71 (quin, J=6.8 Hz, 1H), 4.96 (m, 4H), 7.00-7.30 (m, 6H), 7.50-7.57 (m, 2H), 7.87-7.93 (m, 2H).
$^{31}$P{$^1$H} NMR (C$_6$D$_6$) δ102.4 (s).

NMR Data of Complex K
$^1$H NMR (C$_6$D$_6$) δ0.87 (d, J=7.2 Hz, 6H), 1.88 (s, 3H), 3.03 (quin, J=6.8 Hz, 1H), 4.95-5.02 (m, 4H), 6.98-7.12 (m, 6H), 7.50-7.57 (m, 2H), 7.98-8.02 (m, 2H).
$^{31}$P{$^1$H} NMR (C$_6$D$_6$) δ100.8 (s).

NMR Data of Complex L
$^1$H NMR (C$_6$D$_6$) δ1.25 (s, 15H), 7.07-7.13 (m, 6H), 7.80-7.86 (m, 4H).
$^{31}$P{$^1$H} NMR (C$_6$D$_6$) δ74.4 (s).

TABLE 12

Catalytic performance of complexes J, K and L[a]

| Example | Complex | Solvent | Amount of water (mmol) | Temperature (° C.) | Reaction time (h) | Yield of acrylamide (%) |
|---|---|---|---|---|---|---|
| 12-1 | J | 2-propanol | 4 | 80 | 3.5 | >99 |
| 12-2 | J | water | 4 | 80 | 3.5 | 50 |
| 12-3 | K | 2-propanol | 4 | 80 | 3.5 | >99 |
| 12-4 | K | EtOH | amount of solvent | 80 | 3.5 | 88 |
| 12-5 | K | water | 4 | 80 | 3.5 | 80 |
| 12-6 | L | 2-propanol | 4 | 80 | 3.5 | 35 |
| 12-7 | L | toluene | 4 | 80 | 3.5 | 20 |
| 12-8 | L | EtOH | 4 | 80 | 3.5 | 28 |
| 12-9 | L | water | 4 | 80 | 3.5 | 20 |

[a] Amount used: acrylonitrile: 1 mmol, solvent: 0.5 mL, ruthenium complex: 0.005 mmol (0.5 mol % based on acrylonitrile); Experiment was carried out in argon atmosphere.

The invention claimed is:

1. A hydration catalyst used for hydration reaction comprising a metal complex compound represented by the following general formula (I):

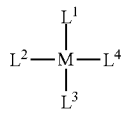
(I)

wherein M is a metal ion selected from the group consisting of ruthenium, osmium, rhodium, iridium, nickel, palladium and platinum, $L^1$ is a cyclic or acyclic, neutral or minus 1-valent unsaturated hydrocarbon group of 1 to 30 carbon atoms which may have a substituent, $L^2$ and $L^3$ are each independently fluorine, chlorine, bromine, iodine, a hydroxyl group, an alkoxy group which may have a substituent or an aryloxy group which may have a substituent, and $L^4$ is a compound bonded to M through phosphorus or arsenic and represented by the following general formula (IIa) or (IIb):

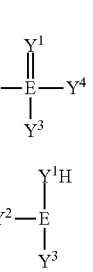
(IIa)

(IIb)

wherein E is phosphorus or arsenic, $Y^1$ is oxygen or sulfur, $Y^2$, $Y^3$ and $Y^4$ are each independently a hydrogen atom, a hydroxyl group, an alkyl group, an aryl group which may have a substituent and a hetero atom other than carbon, an alkoxy group which may have a substituent or an aryloxy group which may have a substituent, and H is a hydrogen atom.

2. A hydration catalyst used for hydration reaction comprising a composite constituted of
a compound represented by the following general formula (III):

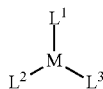
(III)

wherein M is a metal ion selected from the group consisting of ruthenium, osmium, rhodium, iridium, nickel, palladium and platinum, $L^1$ is a cyclic or acyclic, neutral or minus 1-valent unsaturated hydrocarbon group of 1 to 30 carbon atoms which may have a substituent, $L^2$ and $L^3$ are each independently fluorine, chlorine, bromine, iodine, a hydroxyl group, an alkoxy group which may have a substituent or an aryloxy group which may have a substituent, and when the valence of M is +1 or +2, $L^3$ is not present in some cases, and the compound represented by the general formula (III) may form an associate, and a compound represented by the following general formula (IIa) or (IIb):

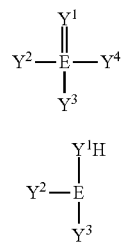
(IIa)

(IIb)

wherein E is phosphorus or arsenic, $Y^1$ is oxygen or sulfur, $Y^2$, $Y^3$ and $Y^4$ are each independently a hydrogen atom, a hydroxyl group, an alkyl group, an aryl group which may have a substituent and a hetero atom other than carbon, an alkoxy group which may have a substituent or an aryloxy group which may have a substituent, and H is a hydrogen atom.

3. The hydration catalyst as claimed in claim 1, wherein $L^1$ is cyclic diene, triene or tetraene of 1 to 30 carbon atoms which may have a substituent and is a neutral or minus 1-valent unsaturated hydrocarbon group.

4. The hydration catalyst as claimed in claim 1, wherein $L^1$ is acyclic diene, triene or tetraene of 1 to 30 carbon atoms which may have a substituent and is a neutral or minus 1-valent unsaturated hydrocarbon group.

5. The hydration catalyst as claimed in claim 1, wherein the compound represented by the general formula (IIa) or (IIb) is any one of secondary phosphine oxide, an aliphatic phosphoric acid ester, an aliphatic phosphorous acid ester, an aromatic phosphoric acid ester and an aromatic phosphorous acid ester of 1 to 30 carbon atoms which may have a substituent.

6. The hydration catalyst as claimed in claim 1, wherein the compound represented by the general formula (IIa) or (IIb) is any one of diarylphosphine oxide which may have a substituent, dialkylphosphine oxide which may have a substituent, secondary phosphine oxide having a phenyl group which may have a substituent and having an alkyl group which may have a substituent, a phosphorous acid dialkyl ester of 1 to 30 carbon atoms, a phosphorous acid diphenyl ester which may have a substituent and a phosphorous acid ester having a phenyl group which may have a substituent and having an alkyl group which may have a substituent.

7. The hydration catalyst as claimed in claim 1, which further comprises a reaction accelerator.

8. The hydration catalyst as claimed in claim 1, wherein the reaction accelerator is any one of diphenylphosphine oxide which may have a substituent, dialkylphosphine oxide which may have a substituent, phosphine oxide having a phenyl group which may have a substituent or an alkyl group which may have a substituent, a phosphorous acid dialkyl ester of 1 to 30 carbon atoms, a phosphorous acid diphenyl ester which may have a substituent, a phosphorous acid ester having a phenyl group which may have a substituent and having an alkyl group which may have a substituent, an aliphatic alcohol which may have a substituent, an aromatic alcohol which may have a substituent, an aliphatic carboxylic acid which may have a substituent and an aromatic carboxylic acid which may have a substituent.

9. The hydration catalyst as claimed in claim 1, which contains the reaction accelerator in an amount of 1 to 100 mol based on 1 mol of the metal complex compound represented by the general formula (I) or the compound represented by the general formula (IIa) or (IIb).

10. The hydration catalyst as claimed in claim 1, which is used for hydration of nitriles.

11. A process for producing amides, comprising:
a step of preparing the catalyst as claimed in claim 1,
a step of adding the catalyst to a mixture of a nitrile and water and/or an organic solvent, and
a step of reacting the mixture containing the catalyst at a temperature of 0 to 150° C. for 0.1 to 48 hours.

12. The process for producing amides as claimed in claim 11, wherein the nitrile is an aliphatic nitrile of 1 to 30 carbon atoms which may have a substituent.

13. The process for producing amides as claimed in claim 11, wherein the nitrile is an aromatic nitrile of 1 to 30 carbon atoms which may have a substituent.

14. The process for producing amides as claimed in claim 12, wherein the nitrile is any one of acrylonitrile, methacrylonitrile, polyacrylonitrile and polymethacrylonitrile.

15. The hydration catalyst as claimed in claim 2, wherein $L^1$ is cyclic diene, triene or tetraene of 1 to 30 carbon atoms which may have a substituent and is a neutral or minus 1-valent unsaturated hydrocarbon group.

16. The hydration catalyst as claimed in claim 2, wherein $L^1$ is acyclic diene, triene or tetraene of 1 to 30 carbon atoms which may have a substituent and is a neutral or minus 1-valent unsaturated hydrocarbon group.

17. The hydration catalyst as claimed in claim 2, wherein the compound represented by the general formula (IIa) or (IIb) is any one of secondary phosphine oxide, an aliphatic phosphoric acid ester, an aliphatic phosphorous acid ester, an aromatic phosphoric acid ester and an aromatic phosphorous acid ester of 1 to 30 carbon atoms which may have a substituent.

18. The hydration catalyst as claimed in claim 2, wherein the compound represented by the general formula (IIa) or (IIb) is any one of diarylphosphine oxide which may have a substituent, dialkylphosphine oxide which may have a substituent, secondary phosphine oxide having a phenyl group which may have a substituent and having an alkyl group which may have a substituent, a phosphorous acid dialkyl ester of 1 to 30 carbon atoms, a phosphorous acid diphenyl ester which may have a substituent and a phosphorous acid ester having a phenyl group which may have a substituent and having an alkyl group which may have a substituent.

19. The hydration catalyst as claimed in claim 2, which further comprises a reaction accelerator.

20. The hydration catalyst as claimed in claim 2, wherein the reaction accelerator is any one of diphenylphosphine oxide which may have a substituent, dialkylphosphine oxide which may have a substituent, phosphine oxide having a phenyl group which may have a substituent or an alkyl group which may have a substituent, a phosphorous acid dialkyl ester of 1 to 30 carbon atoms, a phosphorous acid diphenyl ester which may have a substituent, a phosphorous acid ester having a phenyl group which may have a substituent and having an alkyl group which may have a substituent, an aliphatic alcohol which may have a substituent, an aromatic alcohol which may have a substituent, an aliphatic carboxylic acid which may have a substituent and an aromatic carboxylic acid which may have a substituent.

21. The hydration catalyst as claimed in claim 2, which contains the reaction accelerator in an amount of 1 to 100 mol based on 1 mol of the metal complex compound represented by the general formula (I) or the compound represented by the general formula (IIa) or (IIb).

22. The hydration catalyst as claimed in claim 2, which is used for hydration of nitriles.

23. A process for producing amides, comprising:
a step of preparing the catalyst as claimed in claim 2,
a step of adding the catalyst to a mixture of a nitrile and water and/or an organic solvent, and
a step of reacting the mixture containing the catalyst at a temperature of 0 to 150° C. for 0.1 to 48 hours.

* * * * *

UNITED STATES PATENT AND TRADEMARK OFFICE
CERTIFICATE OF CORRECTION

PATENT NO. : 8,722,912 B2  
APPLICATION NO. : 13/813725  
DATED : May 13, 2014  
INVENTOR(S) : Toshiyuki Oshiki et al.

Page 1 of 1

It is certified that error appears in the above-identified patent and that said Letters Patent is hereby corrected as shown below:

On the Title Page, Item (56), Column 2, OTHER PUBLICATIONS, Line 25, delete "Rutheniurn(II)" and insert -- Ruthenium(II) --

Signed and Sealed this
Twenty-sixth Day of August, 2014

Michelle K. Lee
*Deputy Director of the United States Patent and Trademark Office*